United States Patent
Crowley et al.

(10) Patent No.: US 9,364,445 B2
(45) Date of Patent: *Jun. 14, 2016

(54) STABILIZED COMPOSITIONS CONTAINING ALKALINE LABILE DRUGS

(71) Applicant: Auxilium US Holdings, LLC, Wilmington, DE (US)

(72) Inventors: Michael M. Crowley, Austin, TX (US); Justin M. Keen, Austin, TX (US); John J. Koleng, Austin, TX (US); Feng Zhang, Austin, TX (US)

(73) Assignee: Auxilium US Holdings, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/517,140

(22) Filed: Oct. 17, 2014

(65) Prior Publication Data

US 2015/0057259 A1 Feb. 26, 2015

Related U.S. Application Data

(60) Continuation of application No. 13/463,375, filed on May 3, 2012, now Pat. No. 8,883,187, which is a division of application No. 12/294,367, filed as application No. PCT/US2007/064714 on Mar. 22, 2007, now Pat. No. 8,173,152.

(60) Provisional application No. 60/785,505, filed on Mar. 24, 2006.

(51) Int. Cl.
*A61F 2/02* (2006.01)
*A61K 9/70* (2006.01)
(Continued)

(52) U.S. Cl.
CPC . *A61K 9/70* (2013.01); *A61K 9/006* (2013.01); *A61K 9/703* (2013.01); *A61K 9/7023* (2013.01);
(Continued)

(58) Field of Classification Search
CPC ..... A61K 9/7084; A61K 9/7092; A61L 15/44
See application file for complete search history.

(56) References Cited

U.S. PATENT DOCUMENTS

| 3,017,304 A | 5/1956 | Burgeni |
| RE33,093 E | 10/1989 | Schiraldi |

(Continued)

FOREIGN PATENT DOCUMENTS

| EP | 0250187 | 12/1987 |
| EP | 1493561 | 1/2005 |

(Continued)

OTHER PUBLICATIONS

Final Office Action mailed May 6, 2015 for U.S. Appl. No. 13/903,531.

(Continued)

*Primary Examiner* — Carlos Azpuru
(74) *Attorney, Agent, or Firm* — RatnerPrestia

(57) ABSTRACT

A stabilized bioadhesive composition containing an alkaline labile drug and a method for its preparation are provided. In one aspect, the composition is a hot-melt extruded (HME) composition comprising a preformed excipient mixture comprising an acidic component and an alkaline thermoplastic matrix-forming material, e.g. polymer. The excipient mixture is formed before blending with an alkaline labile drug. The blend is then hot-melt extruded to form the HME composition. By so doing, the acidic component is able to neutralize or render moderately acidic the excipient mixture. This particular process has been shown to substantially reduce the degradation of an alkaline labile drug during hot-melt extrusion. The excipient mixture softens or melts during hot-melt extrusion. It can dissolve or not dissolve drug-containing particles during extrusion. Various functional excipients can be included in the carrier system to improve process performance and/or improve the chemical or physical properties of the HME composition.

15 Claims, 2 Drawing Sheets

(51) Int. Cl.

| | |
|---|---|
| *A61L 15/44* | (2006.01) |
| *A61K 9/00* | (2006.01) |
| *A61K 31/568* | (2006.01) |
| *A61K 45/06* | (2006.01) |
| *A61K 47/10* | (2006.01) |

(52) U.S. Cl.
CPC .............. *A61K 9/7084* (2013.01); *A61K 9/7092* (2013.01); *A61K 31/568* (2013.01); *A61K 45/06* (2013.01); *A61K 47/10* (2013.01); *A61L 15/44* (2013.01); *A61K 9/7069* (2013.01)

(56) References Cited

U.S. PATENT DOCUMENTS

| | | | |
|---|---|---|---|
| 5,095,619 A | 3/1992 | Davis | |
| 5,318,717 A | 6/1994 | Schafer | |
| 5,318,737 A | 6/1994 | Trabert | |
| 5,614,223 A | 3/1997 | Sipos | |
| 5,662,926 A | 9/1997 | Wick | |
| 5,676,969 A | 10/1997 | Wick | |
| 5,679,373 A | 10/1997 | Wick | |
| 5,700,478 A | 12/1997 | Biegajski | |
| 5,766,620 A | 6/1998 | Heiber | |
| 5,851,551 A | 12/1998 | Tseng | |
| 5,939,099 A | 8/1999 | Grabowski | |
| 5,998,431 A | 12/1999 | Tseng | |
| 6,010,715 A | 1/2000 | Wick | |
| 6,048,547 A | 4/2000 | Seth | |
| 6,071,539 A | 6/2000 | Robinson | |
| 6,072,100 A | 6/2000 | Mooney | |
| 6,375,963 B1 * | 4/2002 | Repka .................... | A61K 9/006 424/402 |
| 6,528,089 B1 | 3/2003 | Kothrade | |
| 6,555,131 B1 | 4/2003 | Wolff | |
| 6,562,369 B2 | 5/2003 | Luo | |
| 6,585,997 B2 | 7/2003 | Moro | |
| 6,649,186 B1 | 11/2003 | Robinson | |
| 6,753,370 B2 | 6/2004 | Nakatsukasa | |
| 8,465,759 B2 * | 6/2013 | Crowley ................ | A61K 9/006 264/148 |
| 2003/0110630 A1 | 6/2003 | Onishi | |
| 2003/0141625 A1 | 7/2003 | Shelby | |
| 2005/0058602 A1 | 3/2005 | Ramji | |
| 2005/0100515 A1 | 5/2005 | Sagel | |
| 2005/0169977 A1 | 8/2005 | Kanios | |
| 2005/0281757 A1 | 12/2005 | Ibrahim | |

FOREIGN PATENT DOCUMENTS

| | | |
|---|---|---|
| JP | 63019152 | 1/1988 |
| JP | 2001508037 | 6/2001 |
| JP | 2002248124 | 9/2002 |
| JP | 2004521085 | 7/2004 |
| WO | 9817251 | 4/1998 |
| WO | 9913812 | 3/1999 |
| WO | 0019975 | 4/2000 |
| WO | 0024382 | 5/2000 |
| WO | 0241878 | 5/2002 |
| WO | 03101357 | 12/2003 |

OTHER PUBLICATIONS

Aitken-Nichol et al., "Hot Melt Extrusion of Acrylic Films," Pharmaceutical Research, vol. 13, No. 5, 1996, pp. 804-808.
Apicella et al., "Poly(ethylene oxide) (PEO) and different molecular weight PEO blends monolithic devices for drug release," Biomaterials, 1993, vol. 14, No. 2, pp. 83-90.
Blatz et al., "Interlaminar Adhesives for Coextruding," Paper, Film & Foil Converter, Jan. 1979, pp. 102 and 104.
Crowley, "Physicochemical and Mechanical Characterization of Hot-Melt Extruded Dosage Forms," Dissertation—Presented to the Faculty of the Graduate School of the University of Texas at Austin, May 2003.
Crowley et al, "Stability of polyethylene oxide in matrix tablets prepared by hot-melt extrusion," Biomaterials, 23 (2002) 4241-4248.
De Brabander et al., "Bioavailability of ibuprofen from hot-melt extruded mini-matrices," International Journal of Pharmaceutics 271 (2004) 77-84.
De Brabander et al., "Development and evaluation of sustained release mini-matrices prepared via hot melt extrusion," Journal of Controlled Release, 89 (2003) 235-247.
Entire patent prosecution history of U.S. Appl. No. 13/463,375, filed May 3, 2012, entitled, "Stabilized Compositions Containing Alkaline Labile Drugs."
Huang et al., "Effects of Operational Parameters on the Performance of a Heat-Melt Melt Extruder," The Chinese Pharmaceutical Journal, 2003, 55, 463-472.
McGinty et al., "Hot-Melt Extruded Films for Transmucosal & Transdermal Drug Delivery Applications," Drug Delivery Technology, Sep. 2004, vol. 4, No. 7, pp. 40-47.
Munjal, M., et al., "Chemical Stabilization of a 9-Tetrahydrocannabinol Prodrug in Polymeric Matrix Systems Produced by a Hot-Melt Method: Role of Microenvironment pH", AAPS PharmSciTech, 2006, vol. 7, No. 3.
Repka, M., et al, "Characterization of cellulosic hot-melt extruded films containing lidocaine", European Journal of Pharmaceutics and Biopharmaceutics, Elsevier Science Publishers B.V., Amsterdam, NL., 2004, vol. 59, No. 1, pp. 189-196.
Repka, M., et al, "Influence of Vitamin E TPGS on the properties of hydrophilic films produced by hot-melt extrusion," International Journal of Pharmaceutics, 202 (2000) 63-70.
Zhang et al., "Properties of Hot-Melt Extruded Theophylline Tablets Containing Poly(Vinyl Acetate)," Drug Development and Industrial Pharmacy, 26(9), 931-942 (2000).
Zhang et al., "Properties of Sustained-Release Tablets Prepared by Hot-Melt Extrusion," Pharmaceutical Development and Technology, 4(2), 241-250 (1999).
Entire patent prosecution history of U.S. Appl. No. 12/294,367, filed Sep. 24, 2008, entitled, "Stabilized Compositions Containing Alkaline Labile Drugs," now U.S. Pat. No. 8,173,152, issued May 8, 2012.
Entire patent prosecution history of U.S. Appl. No. 12/294,372, filed Sep. 24, 2008, entitled, "Process for the Preparation of a Hot-Melt Extruded Laminate," now U.S. Pat. No. 8,465,759, issued Jun. 18, 2013.
Entire patent prosecution history of U.S. Appl. No. 13/903,531, filed May 28, 2013, entitled, "Process for the Preparation of a Hot-Melt Extruded Laminate."

* cited by examiner

STABILIZED COMPOSITIONS CONTAINING ALKALINE LABILE DRUGS

CROSS-REFERENCE TO RELATED APPLICATIONS

This application is a continuation application of U.S. patent application Ser. No. 13/463,375, filed May 3, 2012, which is a divisional application of U.S. patent application Ser. No. 12/294,367, filed Sep. 24, 2008, now U.S. Pat. No. 8,173,152, issued May 8, 2012, which is the U.S. National Phase application of PCT International Application No. PCT/US2007/064714, filed Mar. 22, 2007, and claims priority of U.S. Provisional Patent Application No. 60/785,505, filed Mar. 24, 2006, all of which are incorporated herein by reference in their entireties and for all purposes.

FIELD OF THE INVENTION

The present invention concerns a hot-melt extruded (HME) composition comprising an alkaline-labile drug and an alkaline thermoplastic polymer. The invention also concerns a process for preparing a HME pharmaceutical composition having improved drug stability.

BACKGROUND OF THE INVENTION

Buccal delivery of therapeutic agents is a highly desirable alternative mode of administration for drugs that undergo a significant amount of first pass metabolism when administered orally. Steroids, in particular testosterone, are available in transdermal or transmucosal delivery systems.

Testosterone can be admitted transdermally, transmucosally or in a body cavity using a dosage form such as a patch, implant, film, gel, cream, ointment, or suppository. ANDRODERM® (Watson Labs) and TESTODERM® (Alza Corp.) are exemplary extended release transdermal films. According to its PDR package insert, ANDRODERM drug reservoir layer includes testosterone, alcohol, glycerin, glycerol monooleate, methyl laurate, acrylic acid copolymer and water.

Many researchers have utilized hot-melt extrusion techniques to produce pharmaceutical preparations in various forms. Zhang and McGinity utilized hot-melt extrusion to produce sustained release matrix tablets with poly(ethylene oxide) (PEO) and polyvinyl acetate, and more generally non-film preparations with PEO (Zhang, F. and J. W. McGinity, *Properties of Sustained-Release Tablets Prepared by Hot-Melt Extrusion*. Pharmaceutical Development and Technology, 1999. 4(2): p. 241-250; Zhang, F. and J. W. McGinity, *Properties of Hot-Melt Extruded Theophylline Tablets Containing Poly(Vinyl Acetate)*. Drug Development and Industrial Pharmacy, 2000. 26(9): p. 931-942; Robinson, J. R., J. W. McGinity, and P. Delmas, *Effervevescent granules and methods for their preparation*. June 2000 and November 2003, Ethypharm: U.S. Pat. Nos. 6,071,539 and 6,649,186.) Kothrade et al. (Kothrade, S., et al., *Method for producing solid dosing forms*. 2003: U.S. Pat. No. 6,528,089 WO9927916 DE19753298 EP1035841) demonstrated a method of producing solid dosage forms of active ingredients in a vinyllactam co-polymeric binder by hot-melt extrusion. Aitken-Nichol et al. (Aitken-Nichol, C., F. Zhang, and J. W. McGinity, *Hot Melt Extrusion of Acrylic Films*. Pharmaceutical Research, 1996. 13(5): p. 804-808) used hot-melt extrusion methods to produce acrylic polymer films containing the active lidocaine HCl. Grabowski et al. (Grabowski, S., et al., *Solid active extrusion compound preparations containing low-substituted hydroxypropylcellulose*. 1999: U.S. Pat. No. 5,939,099 WO9625151 DE19504832 EP0809488) produced solid pharmaceutical preparations of actives in low-substituted hydroxypropyl cellulose using hot-melt extrusion techniques. Repka and McGinity (Repka, M. A. and J. W. McGinity, *Hot-melt extruded films for transmucosal & transdermal dung delivery applications*. Drug Delivery Technology, 2004. 4(7): p. 40, 42, 44-47) used hot-melt extrusion processes to produce bioadhesive films for topical and mucosal adhesion applications for controlled drug delivery to various mucosal sites (Repka, M. A., S. L. Repka, and J. W. McGinity, *Bioadhesive hot-melt extruded film for topical and mucosal adhesion applications and drug delivery and process for preparation thereof*. Apr. 23, 2002: U.S. Pat. No. 6,375,963; Breitenbach, J. and H. D. Zettler, *Method for producing solid sphereical materials containing a biologically active substance*. 2000: WO 0024382). Robinson et al. produced effervescent granules with controlled rate of effervescence using hot melt extrusion techniques. Breitenbach and Zettler (Breitenbach, J. and H. D. Zettler, *Method for producing solid sphereical materials containing a biologically active substance*. 2000: WO 0024382) produced solid spherical materials containing biologically active substances via hot-melt extrusion. De Brabander et al. (de Brabander, C., C. Vervaet, and J. P. Remon, *Development and evaluation of sustained release mini-matrices prepared via hot melt extrusion*. Journal of Controlled Release, 2003. 89(2): p. 235-247; de Brabander, C., et al., *Bioavailability of ibuprofen from hot-melt extruded mini-matrices*. International Journal of Pharmaceutics, 2004. 271(1-2): p. 77-84) demonstrated sustained release mini-matrices by utilizing hot-melt extrusion techniques.

Various different drugs have been included in HME compositions. Under given circumstances, stable HME compositions can be made. However, the chemical stability of a drug included within the matrix of the HME composition is highly variable when comparing different combinations of matrix-forming material, drugs, excipients and processing conditions.

Various different thermoplastic materials have been used as the matrix-forming material in HME compositions. These materials are generally, but not necessarily, polymeric. One of the more desired polymers for this use is PEO, because PEO-based HME compositions are bioadhesive. They adhere to mucosal tissue when placed in contact with it. Thus, PEO-based HME compositions can be used for transmucosal delivery of therapeutic agents.

U.S. Pat. No. 6,072,100 to Mooney et al. discloses an extruded composition containing "a thermoplastic water-soluble polymer selected from the group consisting of hydroxypropyl cellulose and polyethylene oxide; a water-soluble polymer derived from acrylic acid; medicament; and plasticizer."

U.S. Pat. No. 6,375,963 to Repka et al. discloses a bioadhesive hot-melt extruded film composition comprising a water swellable or water soluble thermoplastic polymer (such as HPC or PEO) and a bioadhesive polymer (such as polycarbophil, carbopol, a co-polymer of methyl vinyl ether and maleic acid or anhydride, one or more acrylic polymers, one or more polyacrylic acids, copolymers of these polymers, a water soluble salt of a co-polymer of methyl vinyl ether and maleic acid or anhydride, a combination thereof and their salts). In some embodiments, the film contains an organic acid, a superdisintegrant, a super-absorbent and/or an antioxidant.

Even with the significant advances in the art provided by the '963 Patent, PEO may be prone to degradation according to the hot-melt extrusion conditions to which it is exposed. The product literature for POLYOX® (the trademark for polyethylene oxide as sold by Dow Chemical) indicates that BHT and vitamin-E (D-α-tocopheryl) are suitable antioxidants for use in stabilizing hot-melt extruded compositions based upon PEO. Huang et al. (*Chinese Pharmaceutical Journal*, (2003) 55/6 (463-472) disclose the advantageous use of parabens and BHT in hot-melt extruded films made from PEO. Repka et al. (*International Journal of Pharmaceutics*, (20 Jul. 2000) 202/1-2, 63-70) disclose the advantageous use of Vitamin E TPGS in hot-melt extruded films made from PEO.

Crowley et al. (*Dissertation Abstracts International*, (2003) Vol. 65, No. 1B, p. 178. Order No.: AAI3119662. 264 pages; *Biomaterials*, (November 2002) Vol. 23, No. 21, pp. 4241-4248) disclose the stabilization of hot-melt extruded films containing PEO as the thermoplastic matrix by inclusion of Vitamin-E-TPGS and Vitamin-E-succinate. The use of low molecular weight PEO as a processing aid for high molecular weight PEO is disclosed. They also disclose that ascorbic acid (0.5-1.0%) degrades PEO during hot-melt extrusion suggesting that ascorbic acid should not be included in formulations containing PEO. Crowley et al. do not disclose the use of testosterone or another steroid in the film.

Moreover, a drug included in a HME composition may also be prone to degradation. For example, testosterone is prone to degradation in alkaline conditions. Its major degradants include 6-beta-hydroxytestosterone, 4-Androsten-16-alpha-ol-3,17-dione, Androstenedione, Epi-testosterone. So, if testosterone, or any other alkaline labile drug were to be included in a HME composition, such a composition would necessarily exclude alkaline materials. Alkaline materials often have desirable physical or clinical properties. So their exclusion from HME compositions is not desirable.

It would be an advancement in the art to develop a method of manufacturing a HME composition comprising an alkaline matrix-forming material and an alkaline labile drug.

SUMMARY OF THE INVENTION

The present invention seeks to overcome some or all of the disadvantages inherent in the above-mentioned compositions and methods. The invention resolves the problem of the instability of alkaline labile drugs, which the inventors have observed during hot-melt extrusion with alkaline or neutral thermoplastic matrices. It has been found that PEO, which is alkaline, can increase the degradation of testosterone during processing. Neutralization of the PEO prior to mixing with the testosterone was found to decrease the amount of impurities formed during hot-melt extrusion.

The inventors have discovered that PEO can be used as the matrix-forming thermoplastic if the PEO is wet or dry granulated with an acidic component and optionally one or more other excipients to form an excipient mixture prior to the addition of an alkaline labile drug. The excipient mixture is then mixed with testosterone and other excipients that can be included in the formulation and then extruded. Therefore, the invention provides a method of preparing a therapeutic stabilized bioadhesive hot-melt extruded composition comprising an alkaline labile drug, an alkaline thermoplastic water soluble or swellable polymer (which is optionally bioadhesive), and an acidic component, the process comprising the steps of: mixing the acidic component with the alkaline thermoplastic, water soluble or swellable polymer to form an excipient mixture, and then blending the excipient mixture with the alkaline labile drug. The mixing step can be wet granulation step.

A key aspect of the invention requires neutralization or moderate acidification of the alkaline thermoplastic polymer (e.g. PEO) with an acidic component. The polymer is neutralized by wet or dry granulating it with the other materials, such as poloxamer, to be included in the matrix, and the acidic component, such as citric acid and/or an acidic polymer, such as CARBOPOL®. Wet granulation is conducted with water (or buffer) or an aqueous alcohol solution. After this excipient mixture has been prepared, it is optionally dried and then blended with the active agent (such as testosterone) followed by hot-melt extrusion of the entire mixture.

When wet granulation is employed to prepare the excipient mixture, an aqueous medium is used. Exemplary aqueous medium includes water, buffer, or water (or buffer) containing organic solvent. In one embodiment, the organic solvent is water miscible. Suitable water miscible solvents include methanol, ethanol, propanol, iso-propanol, benzyl alcohol, cyclomethicone, glycerin, propylene glycol, low molecular weight polyethylene glycol, simethicone, and others known to those of ordinary skill in the art.

The acidic component can be mixed with the alkaline polymer as a liquid or solid. For example, the acidic component may be dissolved, suspended or wet with the aqueous medium used for wet granulation. Alternatively, the acidic component can be added in solid form.

In one embodiment, the acidic component will dissolve during the wet granulation step. In another embodiment, it will not. For example, when the acidic component is an acidic polymer, it may or may not dissolve during wet granulation. It is preferred that the acidic component will at least become hydrated (or wet) with the aqueous medium. In another embodiment, the acidic component is mixed with the alkaline polymer until homogeneity during the wet or dry granulation step.

According to one embodiment, a second matrix forming material, such as poloxamer, a Vitamin E based antioxidant, and an acidic component are wet granulated with the alkaline thermoplastic polymer, such as PEO, to form a neutralized excipient mixture. This mixture is dried (optionally), mixed with drug, and then hot-melt extruded. Alternatively, the second matrix forming material, antioxidant and alkaline thermoplastic polymer are wet granulated and then the acidic component is mixed in to form the neutralized excipient mixture, which is then processed as above.

It has also been found that greater degradation also occurs when the time of exposure of the alkaline labile drug, such as testosterone (Ts), to heat is increased. Thus, another aspect of the invention requires minimizing the heat exposure of testosterone so as to minimize the formation of its degradants during processing. This is done by selecting the appropriate processing conditions to minimize extrusion temperature and duration of extrusion time and to decrease the matrix viscosity.

The composition of the invention can be a film, multi-layered film (laminate), rod, pellet, bead, tablet, pill, granulate, powder, capsule, tube, strand, or cylinder and can be further processed into a powder, pellets, or powder coatings for application on various substrates. A laminate will comprise at least two layers: a bioadhesive drug reservoir layer and a backing layer. In one embodiment, the backing layer of the laminate also includes an acidic component, so as to minimize any interfacial degradation that might occur at the interface of the reservoir layer and the backing layer.

One embodiment of the invention provides a process for preparing a stabilized bioadhesive hot-melt extruded laminate comprising a bioadhesive hydrophilic reservoir layer comprising an alkaline labile drug, an alkaline matrix-forming polymer and an acidic component; and a hydrophobic low permeability backing layer, the process comprising the steps of:

wet or dry granulating at least one water swellable or water soluble alkaline thermoplastic polymer, an antioxidant, at least one bioadhesive polymer, at least one acidic component, optionally one or more hydrophobic polymers, optionally one or more hydrophilic polymers, and optionally one or more other excipients to form an excipient mixture having a solution pH (when dissolved) of about 7 or less or less than the pH where the alkaline labile drug degrades;

mixing the excipient mixture with an alkaline labile drug to form a bioadhesive thermoplastic hydrophilic first composition;

providing a thermoplastic hydrophobic second composition comprising at least one hydrophobic polymer, a plasticizer, optionally one or more hydrophilic polymers, and optionally at least one acidic component;

coextruding the first composition and the second composition to form a bioadhesive bi-layered hot-melt coextruded laminate comprising a bioadhesive hydrophilic reservoir layer and a hydrophobic low permeability backing layer, respectively.

Another aspect of the invention provides a process for preparing a stabilized bioadhesive hot-melt extruded laminate comprising a bioadhesive hydrophilic reservoir layer comprising an alkaline labile drug, an alkaline matrix-forming polymer and an acidic component; and a hydrophobic low permeability backing layer, the process comprising the steps of:

wet or dry granulating at least one water swellable or water soluble alkaline thermoplastic polymer, an antioxidant, at least one bioadhesive polymer, at least one acidic component, optionally one or more hydrophobic polymers, optionally one or more hydrophilic polymers, and optionally one or more other excipients to form an excipient mixture having a solution pH (when dissolved) of about 7 or less or less than the pH where the alkaline labile drug degrades;

mixing the excipient mixture with an alkaline labile drug to form a bioadhesive thermoplastic hydrophilic first composition;

providing a thermoplastic hydrophobic second composition comprising at least one hydrophobic polymer, a plasticizer, optionally one or more hydrophilic polymers, and optionally at least one acidic component;

extruding the first composition to form a bioadhesive hydrophilic reservoir layer;

extruding the second composition to form a hydrophobic low permeability backing layer; and laminating the reservoir layer to the backing layer to form the laminate.

Yet another aspect of the invention provides a process for preparing a stabilized bioadhesive bilayered laminate comprising a bioadhesive hydrophilic reservoir layer comprising an alkaline labile drug, an alkaline matrix-forming polymer and an acidic component; and a hydrophobic low permeability backing layer, the process comprising the steps of:

wet or dry granulating at least one water swellable or water soluble alkaline thermoplastic polymer, an antioxidant, at least one bioadhesive polymer, at least one acidic component, optionally one or more hydrophobic polymers, optionally one or more hydrophilic polymers, and optionally one or more other excipients to form an excipient mixture having a solution pH (when dissolved) of about 7 or less or less than the pH where the alkaline labile drug degrades;

mixing the excipient mixture with an alkaline labile drug to form a bioadhesive thermoplastic hydrophilic first composition;

extruding the first composition to form a bioadhesive hydrophilic reservoir layer;

providing a thermoplastic hydrophobic second composition comprising at least one hydrophobic polymer, a plasticizer, optionally one or more hydrophilic polymers, and optionally at least one acidic component; and either hot-melt extruding the second composition onto the reservoir layer to form a bioadhesive bi-layered laminate;

hot-melt extruding the second composition to form a hydrophobic low permeability backing layer and subsequently laminating the reservoir layer and the backing layer together to form a bioadhesive bi-layered laminate; or casting the second composition onto the reservoir layer to form a bioadhesive bi-layered laminate.

Another aspect of the invention provides a process for the preparation of a stabilized bioadhesive hot-melt extruded composition comprising an alkaline labile drug, an alkaline matrix-forming polymer and an acidic component, the process comprising:

wet or dry granulating at least one water swellable or water soluble alkaline thermoplastic polymer, an antioxidant, at least one bioadhesive polymer, at least one acidic component, optionally one or more hydrophobic polymers, optionally one or more hydrophilic polymers, and optionally one or more other excipients to form an excipient mixture having a solution pH (when dissolved) of about 7 or less or less than the pH where the alkaline labile drug degrades;

mixing the excipient mixture with an alkaline labile drug to form a bioadhesive thermoplastic hydrophilic composition; and hot-melt extruding the hydrophilic composition to form the bioadhesive hot-melt extruded composition.

The compositions can be optionally dried, as appropriate, either prior to the addition of the alkaline labile drug and/or prior to extrusion. For example, the excipient mixture can be dried prior to conducting mixing with the alkaline drug or the bioadhesive thermoplastic hydrophilic composition can be dried prior to hot-melt extrusion.

The wet granulation can be conducted with water, buffer, or aqueous alcohol. The granulation fluid optionally contains an acidic component.

The acidic component can be an acidic polymer (such as a bioadhesive polymer), inorganic acid, mineral acid or an organic acid or mixtures thereof. For example, the bioadhesive polymer can be the acidic component.

The wet granulation step can be conducted in various different ways. For example, the wet granulation step can be conducted by first wet granulating a poloxamer, an antioxidant, PEO and an organic acid and then adding a bioadhesive polymer. Alternatively, the wet granulation step can be conducted by first mixing an aqueous solution of organic acid and hydrophilic polymer with an alcohol solution of antioxidant and then adding PEO and then adding a bioadhesive polymer.

The composition of the bioadhesive thermoplastic hydrophilic composition can vary. For example, it can comprise two or more thermoplastic and water swellable, water soluble or water erodible polymers, and/or it can comprise two or more water swellable, water erodible or water soluble alkaline thermoplastic polymers. PEO is an exemplary bioadhesive alkaline thermoplastic water soluble or water erodible polymer. In some embodiments, the water swellable or water soluble alkaline thermoplastic polymer is a bioadhesive polymer.

The composition of the excipient mixture can vary. For example, a hydrophilic polymer can be present in the excipient mixture, another hydrophobic polymer can be present in the excipient mixture.

The composition of the backing layer can vary. For example, it can comprise two or more different hydrophobic polymers.

In some embodiments, the laminating step is heat-catalyzed lamination, and/or the laminating step comprises the steps of placing an adhesive between the reservoir layer and the backing layer followed by pressing of the two layers together.

If the reservoir and backing layers of the laminate are coextruded or extruded individually (be it sequentially or concurrently) and subsequently laminated, the layers preferably comprise at least one polymer in common; however, the layers will retain their individual characteristics of hydrophobicity and hydrophilicity. The reservoir and backing layers optionally possess approximately the same melt flow index (melt flow rate, melt flow rate, melt index, meaning that their melt flow indices will fall within individual predefined ranges and that those ranges overlap at least to some predefined extent.

When the HME composition includes testosterone, it can be used to treat one or more disorders associated with testosterone deficiency, e.g. hypogonadism, Peyronie's disease, priapism, impotence, erectile dysfunction, reduced libido, loss of muscle mass, etc. The method of use includes the transdermal, preferably the buccal, administration of a bioadhesive hot-melt extruded composition comprising testosterone in controlled release form. During use, the bioadhesive layer absorbs water from saliva and begins to release testosterone in a controlled manner.

The HME composition can be formulated to provide a variety of drug release profiles to most sites of administration.

The present invention also includes pharmaceutical formulations comprised of active compounds finely and homogenously dispersed in one or more polymeric carriers that are produced by hot-melt extrusion techniques. Such preparations can include solid dispersions, glass solutions, molecular dispersions, and solid solutions. The invention also provides pharmaceutical formulations wherein the active agent (active compound) is provided in neat form (meaning not containing excipients) and subsequently employed in the process as detailed herein.

In some embodiments, the pharmaceutical composition is formulated such that drug therein may be dissolved during extrusion.

Fine particles of drug made by known processes can be incorporated into the claimed pharmaceutical composition. Examples include micronization and milling processes. Drug-containing particles are dispersed within the matrix via hot-melt extrusion.

In some embodiments, the thermoplastic matrix-forming material is selected from the group consisting of polyethylene oxide; polypropylene oxide; polyvinylpyrrolidone; polyvinylpyrrolidone-co-vinylacetate; PLA, PLGA, acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, sucrose stearate, xanthan gum, lipids, waxes, mono, di, and tri glycerides, cetyl alcohol, steryl alcohol, paraffin waxes and the like, hydrogenated vegetable and castor oil, glycerol monostearte, enteric polymers such as CAP, HPMC AS, shellac, and a combination thereof.

Release of drug from the HME composition can vary. In some embodiments, the composition (or dosage form) provides an immediate or rapid release of therapeutic compound after exposure to an environment of use. In other embodiments, the pharmaceutical composition (or dosage form) provides a delayed release of therapeutic compound after exposure to an environment of use.

The pharmaceutical dosage form or composition described herein can be formulated for transdermal, transmucosal, buccal, rectal, pulmonary, nasal, vaginal, ocular, peroral, oral, intestinal or otic drug delivery, or as an implantable drug delivery device.

The invention also includes combinations of two or more of the different embodiments disclosed herein.

BRIEF DESCRIPTION OF THE FIGURES

The following figures form part of the present description and describe exemplary embodiments of the claimed invention. The skilled artisan will be able, in light of these figures and the description herein, to practice the invention without undue experimentation.

DETAILED DESCRIPTION OF THE INVENTION

The invention provides a stabilized HME composition comprising an alkaline-labile drug, a thermoplastic bioadhesive matrix, an acidic component and optionally one or more excipients. The matrix comprises one or more alkaline thermoplastic polymers, one or more bioadhesive polymers, or a combination thereof. The HME composition comprises a bioadhesive hot-melt extrudable excipient composition comprising an alkaline thermoplastic bioadhesive polymeric matrix, an acidic component and optionally one or more excipients, wherein the excipient composition has a solution pH of 7.0 or less when placed in water. When an alkaline thermoplastic bioadhesive matrix is mixed with an acidic component it will form a non-alkaline thermoplastic bioadhesive matrix, meaning that the matrix will have a pH of 7 or less when placed in water. The excipient composition has a neutral to moderately acidic pH (2-7). An alkaline labile drug, and optionally one or more other excipients, is mixed with the excipient composition, and the mixture is hot-melt extruded to form the stabilized HME composition.

The term hot-melt extrusion or hot-melt extruded is used herein to describe a process whereby a composition is heated and/or compressed to a molten (or softened) state and subsequently forced through an orifice in a die where the extruded product is formed into its final shape in which it solidifies upon cooling. The blend is conveyed through one or more heating zones typically by a screw mechanism. The screw or screws are rotated by a variable speed motor inside a cylindrical barrel where only a small gap exists between the outside diameter of the screw and the inside diameter of the barrel. In this conformation, high shear is created at the barrel wall and between the screw fights by which the various components of the powder blend are well mixed and disaggregated. The die can be a dual manifold, multi-manifold or feedblock style die. As used herein, the term extrudate refers to a HME composition. The term "coextrusion" is taken to mean an extrusion process in which at least two different melt compositions are extruded substantially simultaneously through a dual confining orifice to form respective first and second layers of a laminate, whereby the sum total cross-sectional area of the two layers corresponds substantially to the cross-sectional area of the exit orifice in the extrusion die. The term "lamination" is taken to mean an extrusion process in which at least two different layers are hot-melt extruded and combined after exiting the extrusion orifice and then bonded by a set of opposing rollers.

The term "hot-melt extrudable" is taken to mean that a material or composition can be hot-melt-extruded with no significant thermal degradation, e.g. less than 5% wt. or less than 10% wt. degradation. The term "thermally processable" is taken to mean a material or composition that softens or melts at the extrusion processing temperature with no significant thermal degradation.

Figure 1:
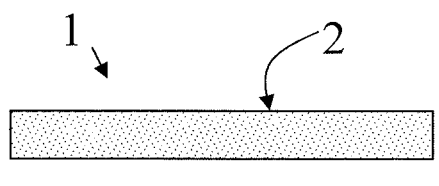
FIG. 1 depicts a cross-sectional front elevation of an exemplary embodiment of a mono-layered hot-melt extruded composition according the invention.

FIG. 1 depicts a conceptual cross-sectional front elevation of an exemplary monolithic hot-melt extruded composition (1) comprising a drug reservoir (2) according to the invention. The extrudate prepared as detailed herein provides improved stability of an alkaline labile drug within a matrix comprising an alkaline thermoplastic polymer. The drug reservoir comprises an alkaline labile drug and a bioadhesive thermoplastic matrix, wherein the matrix comprises an acidic component (or acidifying agent), an alkaline polymer, a bioadhesive polymer, a thermoplastic polymer, and optionally one or more other excipients. In other words, the matrix comprises an alkaline thermoplastic and/or bioadhesive matrix-forming material, an acidic component and optionally one or more other excipients.

The matrix of the present pharmaceutical composition includes a matrix-forming material such as a thermal binder, a pressure softenable binder, or a combination thereof. At least one polymeric binder in the matrix is a bioadhesive polymer. At least one polymer in the matrix is an alkaline polymer prior to treatment with an acidic component.

Exemplary thermal binders include: polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; PLA and PLGA, polyesters (shellac), wax such as carnauba wax, beeswax; polysaccharides such as cellulose, tragacanth, gum arabic, guar gum, and xanthan gum.

A specific embodiment of the binder is poly(ethylene oxide) (PEO), which can be purchased commercially from companies such as the Dow Chemical Company and Sumitomo Seika, which market PEO exemplary grades with an average molecular weight from about 100,000 to about 8,000,000. Some of the grades of PEO that are suitable for use in this invention are described in the tables below, which differentiate the grades according to their approximate molecular weights and solution viscosity.

| Trade Name | Approximate Molecular Weight | Viscosity Range Aqueous Solution at 25° C., mPa · s |
|---|---|---|
| WSR N-10 | 100,000 | 30-50 (5% solution) |
| PEO-1Z | 150,000-400,000 | 50-200 (5% solution) |
| WSR N-80 | 200,000 | 55-90 (5% solution) |
| WSR N-750 | 300,000 | 600-1,200 (5% solution) |
| WSR N-3000 | 400,000 | 2250-4500 (5% solution) |
| WSR-205 | 600,000 | 4,500-8,800 (5% solution) |
| PEO-3Z | 600,000-1,100,000 | 2,500-5,500 (5% solution) |
| WSR-1105 | 900,000 | 8,800-17,600 (5% solution) |
| WSR N-12K | 1,000,000 | 400-800 (2% solution) |
| PEO-8Z | 1,700,000-2,200,000 | 20-70 (0.5% solution) |
| WSR N-60K | 2,000,000 | 2,000-4,000 (2% solution) |
| PEO-15Z | 3,300,000-3,800,000 | 130-250 (0.5% solution) |
| WSR-301, UCARFLOC Polymer 300 | 4,000,000 | 1,650-5,500 (1% solution) |
| PEO-18Z | 4,300,000-4,800,000 | 250-430 (0.5% solution) |
| WSR Coagulant, UCARFLOC Polymer 302 | 5,000,000 | 5,500-7,500 (1% solution) |
| WSR-303, UCARFLOC Polymer 304 | 7,000,000 | 7,500-10,000 (1% solution) |
| PEO-27 | 6,000,000-8,000,000 | 600-800 (0.5% solution) |
| WSR-308, UCARFLOC Polymer 309 | 8,000,000 | 10,000-15,000 (1% solution) |

In general, any PEO material described herein or any known PEO having the characteristics of a PEO material as described herein can be used.

In one embodiment, the term "PEO Grade 1" is taken to mean a polyethylene oxide with a solution viscosity in the range of 12-8800 mPa·s at 25° C. in a 5% solution or approximate molecular weight range from 100,000-600,000. Examples of Grade 1 PEOs are listed in the table above and include POLYOX WSR N-10, WSR N-80, WSR N-750, WSR N-3000, WSR N-205 or equivalents thereof.

In one embodiment, the term "PEO Grade 2" is taken to mean a polyethylene oxide with a solution viscosity in the range of 8800 mPa·s at 25° C. in a 5% solution to 4000 mPa·s at 25° C. in a 2% solution or approximate molecular weight range from 900,000-2,000,000. Examples of Grade 2 PEOs are listed in the table above and include POLYOX WSR N-1105, WSR N-12K, WSR N-60, or equivalents thereof.

In one embodiment, the term "PEO Grade 3" is taken to mean a polyethylene oxide with a solution viscosity in the range of 1650-15,000 mPa·s at 25° C. in a 1% solution or approximate molecular weight range from 4,000,000-8,000,000. Examples of Grade 3 PEOs are listed in the table above and include POLYOX WSR 301, WSR Coagulant, WSR 303, WSR 308, or equivalents thereof.

PEO Grade 1, PEO Grade 2 and/or PEO Grade 3 can occur in the drug reservoir layer, the inert backing layer or both layers. In the embodiment wherein a particular grade of PEO occurs in the reservoir layer and the inert backing layer, that grade of PEO is independently selected at each occurrence from its respective definition. In other words, if PEO Grade 1 occurs in the reservoir layer and the backing layer, then it will be selected at each occurrence from the above-specified group for PEO Grade 1. Likewise for PEO Grade 2 and PEO Grade 3.

When three grades of PEO are included in the same layer, PEO Grade 3 has a higher viscosity than PEO Grade 2, which has a higher viscosity than PEO Grade 1. When two grades of PEO are included in the same formulation, there are several possible combinations: a) PEO Grade 3+PEO Grade 2, wherein PEO Grade 3 has a higher viscosity than PEO Grade 2; b) PEO Grade 3+PEO Grade 1, wherein PEO Grade 3 has a higher viscosity than PEO Grade 1; and c) PEO Grade 2+PEO Grade 1, wherein PEO Grade 2 has a higher viscosity than PEO Grade 1.

When three different grades of PEO are present, the amount of each ranges from 5 to 50% by wt. of the layer. The total amount of PEO present generally ranges from about 10% to about 70%, about 20% to about 70%, about 30% to about 70%, or about 40% to about 70% by wt. of the reservoir layer. Some embodiments of the reservoir layer include those wherein the total amount of PEO is about 64%, 43.64%, 61.5%, 59%, 62.5%, 63%, 65.82%, 60.82% by wt. of the reservoir layer.

The total amount of PEO present generally ranges from 0% to about 60%, about 10% to about 60%, about 20% to about 60% or about 40% to about 60% by wt. of the backing layer. Some embodiments of the backing layer include those wherein the total amount of PEO is about 10%, 35%, 50%, 54%, 56%, 58% by weight of the backing layer.

In some embodiments, the amount of PEO Grade 1 ranges from 5 to 50% by wt. of the layer, such as 5%, 10%, 26.85%, 27.9%, 23.67%, 32.9%, 36.01%, 34%, 38.16%, 33.86% of the layer; the amount of PEO Grade 2 ranges from 5 to 50% by wt. of the layer, such as 5%, 22.18%, 21.16%, 26.16%, 20.36%, 28.64%, 27%, 30.35%, 14.96%, 15.91%, 18.36%, 18.86%, 19.36%, 7.5% of the layer; and the amount of PEO Grade 3 ranges from 5 to 50% by wt. of the layer, such as 13.79%, 16.29%, 16.79%, 17.44%, 19.1%, 18%, 20.24%, 29.93%, 31.83%, 36.5%, 45% wt. of the layer.

When any type or class of material is present in both the reservoir and the backing layer, it will be independently selected at each occurrence from the list of suitable materials described herein or known to the artisan in the field of pharmaceutics. For example, if PEO is present in both the reservoir layer and the backing layer, the grade or grades of PEO used in reservoir layer will be selected at each occurrence independently of the grade or grades of PEO used in the backing layer.

Suitable thermal binders that may or may not require a plasticizer include, for example, Eudragit™ RS PO, Eudragit™ S100, Kollidon SR (poly(vinyl acetate)-co-poly(vinylpyrrolidone)copolymer), HPC (hydroxypropylcellulose), cellulose acetate butyrate, poly(vinylpyrrolidone) (PVP), poly(ethylene glycol) (PEG), poly(ethylene oxide) (PEO), poly(vinyl alcohol) (PVA), hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.), cellulose acetate phthalate (CAP), cellulose acetate trimelletate (CAT), polyesters (shellac), waxes (carnauba wax, beeswax), poly(vinyl acetate) phthalate (PVAP), hydroxypropylmethylcellulose phthalate (HPMCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit™ L100 (MA-EA, 1:1), Eudragit™ L-100-55 (MA-EA, 1:1), hydroxypropylmethylcellulose acetate succinate (HPMCAS), Coateric™ (PVAP), starches, pectins; polysaccharides such as cellulose, tragacanth, gum arabic, guar gum, sugars and xanthan gum.

Some of the above-noted binders are bioadhesive alkaline thermoplastic polymers. The matrix of the invention can include a combination of materials, some of which are not alkaline, not bioadhesive, or not thermoplastic. It is only important that the matrix (e.g., the excipient mixture) retain its bioadhesive thermoplastic nature prior to hot-melt extrusion and retain its bioadhesive nature after hot-melt extrusion.

Other polymeric materials that can be included in the matrix include cellulosic polymers including HPMC, HPC, methylcellulose; polyvinyl alcohol, polyvinylpyrrolidone, polyvinylpyrrolidone-co-vinyl acetate and other polymers approved for pharmaceutical use known to those of ordinary skill in the art.

The alkaline bioadhesive thermoplastic matrix can further comprise other materials, in particular other polymers such as KLUCEL (hydroxypropylcellulose), CARBOPOL, POLYCARBOPHIL GANTREZ, POLOXAMER, and combinations thereof. The product literature for CARBOPOL® indicates that aqueous solutions containing it have a pH in the range of 2.5-4.0, meaning it is an acidic polymer and not considered an alkaline polymer; however, it is a bioadhesive polymer. GANTREZ® is a copolymer of methyl vinyl ether and maleic anhydride, and its solution pH will depend upon the form in which it is provided. GANTREZ® MS is a mixed calcium and sodium salt of the polymer having a solution pH between 5.5-7.0. GANTREZ® is a bioadhesive polymer but not a thermoplastic polymer. The product literature for POLYCARBOPHIL®, high molecular weight, cross-linked, acrylic acid-based polymers, indicates that aqueous solutions containing it have a pH less than 4.0, meaning it is an acidic polymer and not considered an alkaline polymer; however, it is a bioadhesive polymer. POLOXAMER® 407 is a block copolymer of ethylene glycol and propylene glycol and according to the product literature it has a solution pH of 6.0-7.4. POLOXAMER® is not considered a bioadhesive polymer and it is not a thermoplastic polymer.

An extrudate composed of PEO and POLOXAMER can form a homogeneous polymer matrix when melt extruded at 100° C. Compositions further comprising HPMC, PVA, or SLS can be made.

The matrix or excipient mixture can contain one or more bioadhesive polymers, one or more thermoplastic polymers and/or one or more alkaline polymers. In one embodiment, the alkaline polymer is also the bioadhesive polymer. In another embodiment, the alkaline polymer is also the thermoplastic polymer. In still another embodiment, the bioadhesive polymer is the thermoplastic polymer. Yet another embodiment includes an alkaline polymer that is a bioadhesive polymer and a thermoplastic polymer, wherein, in other words, a single polymer is bioadhesive, thermoplastic and alkaline prior to hot melt extrusion. Examples of such polymers include polyethylene oxide, hydroxypropylcellulose, hydroxyethylcellulose, hydroxypropyl methylcellulose, povidone and others known to one of ordinary skill in the art.

The hot-melt extrusion equipment is typically a single or twin-screw apparatus, but can be composed of more than two screw elements. A typical hot-melt extrusion apparatus contains a mixing/conveying zone, a heating/melting zone, and a pumping zone in succession up to the orifice. In the mixing/conveying zone, the powder blends are mixed and aggregates are reduced to primary particles by the shear force between the screw elements and the barrel. In the heating/melting zone, the temperature is at or above the melting point or glass transition temperature of the thermal binder or binders in the blend such that the conveying solids become molten as they pass through the zone. A thermal binder in this context describes an inert excipient, typically a polymer, that is sufficiently solid at ambient temperature, but becomes molten, softened or semi-liquid when exposed to elevated heat or pressure. The thermal binder acts as the matrix in which the active or actives and other functional ingredients are dispersed, or the adhesive with which they are bound such that a continuous composite is formed at the outlet orifice. Once in a molten state, the homogenized blend is pumped to the orifice through another heating zone that maintains the molten state of the blend. At the orifice, the molten blend can be formed into strands, cylinders or films. The extrudate that exits is then solidified typically by an air-cooling cooling process. The extrudate can be a single layer or it can be a coextruded laminate or a bi-layered, tri-layered or multi-layered laminate formed by laminating two or more layers together. Once solidified, the extrudate may then be further processed to form pellets, spheres, fine powder, tablets, and the like. An example of a single screw apparatus similar to the description above is the Randcastle Taskmaster, model 1 inch, 36:1.

Temperature is an important process variable to consider for the hot-melt extrusion. The composition can be HME at any temperature desired provided it does not result in excessive degradation of the composition or any of it components.

Other process variables such as feed rate and screw speed are optimized to provide adequate shear and mixing. The effect of feed rate and screw speed on such dependent variables as the level of shear and mixing inside the extruder depends heavily on the design of the equipment and namely the screw elements. Generally, increasing the screw speed will increase the shear forces between the screw element and the barrel wall, thereby allowing for more rigorous mixing and a greater extent of particle disaggregation. Decreasing the feed rate (non-flood feeding) will generally allow for more complete mixing and particle disaggregation due a reduction in the amount of material within the extruder. Reducing the amount of material will in turn also increase the shear forces the material is subjected to due to a decrease in the effective channel depth.

It is also important to consider the ways in which the components of a formulation are fed to the extruder. One method is to pre-blend all formulation components before being fed to the extruder. This can be done by any traditional mixing or blending technique. Alternatively, formulation components may be fed individually if done simultaneously, and given that there is adequate mixing of the formulation components in the mixing/conveying zone of the extruder. For example, the drug is mixed with the excipient composition after formation of the excipient composition. The blend is then hot-melt extruded. Furthermore, components other than the base polymers may also be fed downstream of the initial feed port to reduce their residence time in the extruder given that there is adequate mixing of the formulation components before and in the last mixing zone. For example, an excipient blend may be fed at the initial feed port and a heat sensitive component may be fed prior to the last zone to minimize the time of heat exposure. Additionally, a solid non-melting component that significantly increases the melt viscosity may be fed downstream to reduce the amount of energy required to rotate the extruder screw.

The excipient mixture of the invention can be prepared by a variety of different methods. A key aspect to its preparation is contact of the acidic component with the bioadhesive alkaline thermoplastic polymer. One particular method is wet or dry granulation. In one embodiment, the excipient mixture is prepared by wet granulating the bioadhesive alkaline thermoplastic polymer and the acidic component, and optionally one or more other excipients, in the presence of an aqueous medium. The excipient mixture is optionally dried after wet granulation. Therefore, the dry or wet excipient mixture is mixed with drug, and optionally one or more other excipients, to form a blend that is then hot-melt extruded. The aqueous medium can be added in portions or in a bolus. In one embodiment, the alkaline polymer and the acidic polymer are wet granulated and then a second bioadhesive polymer is added to the granulate to prepare the excipient mixture.

One embodiment of the invention requires pre-formation of the excipient mixture prior to mixing with the alkaline labile drug. Other embodiments require formation of the excipient composition by wet granulation with an aqueous liquid, wherein the aqueous liquid optionally comprises alcohol.

The HME composition of the invention is made according to a process as described herein. Exemplary formulations and processes for their preparation are detailed in the examples below.

The monolithic matrix of FIG. 1 is made by hot-melt extruding a blend comprising an excipient composition and an alkaline labile drug. General methods for hot-melt extrusion are detailed herein and in Example 1.

The advantages of the present process of the invention can be exemplified by evaluation of hot-melt extruded compositions containing testosterone as the exemplary alkaline labile drug. The compositions were prepared as described herein. Various processing variables were evaluation to determine their influence upon the stability of the drug to hot-melt extrusion conditions.

Testosterone obtained commercially (for example, from Diosynth a Division of Akzo Nobel, Arnhem, The Netherlands) already includes or can include a number of different impurities such as 6-beta-hydroxytestosterone, 4-Androsten-16-alpha-ol-3,17-dione, Androstenedione, Epi-testosterone, which impurities are present in varying amounts. Some of these impurities are formed by virtue of the synthetic process to prepare testosterone and others are formed due to degradation of the testosterone. During HME of a hot-melt extrudable alkaline thermoplastic matrix containing testosterone, the drug might undergo degradation thereby producing new degradants or increasing the amounts of degradants already present.

The influence of the order of mixing of formulation components upon the stability of testosterone toward degradation during HME was evaluated. In Lot A, all of the formulation components were mixed (blended, granulated or slugged) in dry form to form a blend, which was subsequently extruded. In Lot B, all of the formulation components were mixed in the presence of a liquid to form a wet granulate, that was optionally dried prior to HME.

Formulations made according to the process of the invention, however, demonstrated a significant reduction in the extent of testosterone degradation occurring during HME. Prior to addition of an acidic component, the thermoplastic bioadhesive matrix (or polymer) has a solution pH greater than 7 or ranging from about pH 8 to about pH 10. Following addition of the acidic component to the matrix, the excipient mixture has a solution pH of 7 or less or about pH 2.5 to pH 7. Exemplary lots of the excipient mixture were made according to the invention. In Lot C, the alkaline thermoplastic matrix-forming material was dry granulated with the acidic component, and optionally one or more other excipients, to form an excipient mixture having a solution pH (when dissolved) of about 7 or less or less than the pH where testosterone degrades during HME (See Example 1). The excipient mixture was then mixed with testosterone and optionally other excipients to form a uniform blend (See Example 2) that is hot-melt extruded. In Lot D, the alkaline thermoplastic matrix-forming material was wet granulated with the acidic component, and optionally one or more other excipients, to form an excipient mixture having a solution pH (when dissolved) of about 7 or less or less than the pH where testosterone degrades during HME (See Example 1). The excipient mixture was then mixed with testosterone and optionally other excipients to form a uniform blend (See Example 2) that is hot-melt extruded. Accordingly, HME compositions prepared according to the invention comprise lower amounts of impurities than do similar compositions comprising the same components but made without preformation of an excipient mixture.

| Lot No. | Total Unknown Impurities (%) | 6B-Hydroxy-testosterone (%) | 4-Androsten-16-alpha-ol-3,17-dione (%) | Epi-Testosterone[b] (%) |
|---|---|---|---|---|
| A | 0.20-4.50 | 0.05-1.50 | 0.05-1.50 | 0.00-1.50 |
| B | 0.20-4.50 | 0.05-1.50 | 0.05-1.50 | 0.00-1.50 |
| C | 0.00-2.00 | 0.00-0.50 | 0.00-0.50 | 0.00-0.50 |
| D | 0.00-2.00 | 0.00-0.50 | 0.00-0.50 | 0.00-0.50 |

[b]Epi-testosterone (cis-testosterone) is a concomitant component of testosterone (Per USP<1086>) Concomitant components are characteristics of many bulk pharmaceutical chemicals and are NOT considered to be degradants.

The influence of having more than one type of acidic component upon the stability of testosterone to degradation during HME was evaluated. Lot 56 incorporated citric acid as a secondary acidifier and butylated hydroxytoluene as an antioxidant in place of Vitamin E succinate. The lot was prepared by wet granulating the PolyOx and Poloxamer with 5% water under high shear. Carbopol was added and blended until uniform. Testosterone and the remaining ingredients were added and blended under high shear. The blend was extruded as a monolayer film using the Randcastle at 135° C. and 145° C. The moisture content of the blend prior to extrusion was 3.1%. Following extrusion, the film was cut into unit dose. Composites of 10 doses were analyzed for impurities in duplicate. The table below includes the results.

| Lot No./ Temp. (° C.) | Total Unknown Impurities (%) | 6B-Hydroxy-testosterone (%) | 4-Androsten-16-alpha-ol-3,17-dione (%) | Epi-Testosterone[b] (%) |
|---|---|---|---|---|
| No. 56 135° C. | 1.2 | ND | ND | ND |
| No. 56 145° C. | 1.1 | ND | ND | ND |

ND denotes below the limit of quantitation using the HPLC method detailed herein. In this case, ND means less than 0.1% by wt.

In Lot 61 the antioxidant content was increased to 4% by wt. and the Poloxamer content was increased to 6% by wt. The blend was wet granulated with water at 5% and extruded using the Randcastle at 135° C. Degradant levels were determined by HPLC and results are included in the table above. The Poloxamer content was increased to 7.5% in Lot 62 and to 9% in Lot 63. The blends were wet granulated with water at 5% and extruded using the Randcastle at 135° C.

The influence of HME temperature upon degradation of testosterone was evaluated. A HME composition was prepared by wet granulating PolyOx and Poloxamer with water under high shear. Carbopol was added and blended until uniform. Testosterone and the remaining ingredients were added and blended under high shear. These blends were extruded as a monolayer film using the Randcastle at 135° C. or 145° C. The moisture content of the blend prior to extrusion was 3.1%. The purity profile of the resulting extrudates was determined. The table below indicates the results.

| Temp (° C.) | Total Unknown Impurities (%) | 6B-Hydroxy-testosterone (%) | 4-Androsten-16-alpha-ol-3,17-dione (%) | Epi-Testosterone[b] (%) |
|---|---|---|---|---|
| 135 | 0.1 | ND | ND | ND |
| 145 | 0.4 | 0.15 | ND | ND |

The influence of wet granulation technique (water addition rate, acidification time and water content) on testosterone stability was investigated. The rate of water addition was studied by applying a "BOLUS" loading versus "SERIAL" addition (sequential addition of portions). One lot was prepared using the bolus technique in which the entire water loading (5% based upon solids) was added in one step to the PolyOx, Poloxamer and Carbopol polymers under high shear. Another lot was prepared by the serial technique in which the water and Carbopol loadings were incorporated into the PolyOx and Poloxamer polymers in 4 separate steps. The results indicate a slightly lower degree of degradant formation when the granulation liquid is added as a bolus loading.

The effect of the quantity of water, used as the liquid medium during wet granulation, upon drug stability was investigated. One lot was prepared using the bolus technique with 7.5% water loading, which is a higher water loading. A reduction in major impurities was observed using higher water loading. A water loading of up to 98% can be used provided the extruder is equipped to handle the increased amounts of steam formed using feed mixtures having high water content.

The influence that use of a hydroalcoholic granulation solution during granulation has upon drug stability was studied. In one lot, a 50:50 water/ethanol solution (10% based upon solids) was used to wet granulate the polymers. The resultant granules were dried at 60° C. to an LOD (loss on drying) of less than 3.1% prior to further processing. A lower concentration of degradants was present in the HME composition when using the hydroalcoholic granulation solution as compared to use of just water as the granulation solution. The ratio of water to water miscible solvent in the granulation solution can range from 5:95 to 95:5.

| Granulation Fluid | Total Unknown Impurities (%) | 6B-Hydroxy-testosterone (%) | 4-Androsten-16-alpha-ol-3,17-dione (%) | Epi-Testosterone[b] (%) |
|---|---|---|---|---|
| Water | 0.50-1.00 | 0.10-0.50 | 0.10-0.50 | 0.00-0.50 |
| Aqueous Ethanol | 0.00-0.75 | 0.00-0.20 | 0.00-0.20 | 0.00-0.50 |

Figure 4A:
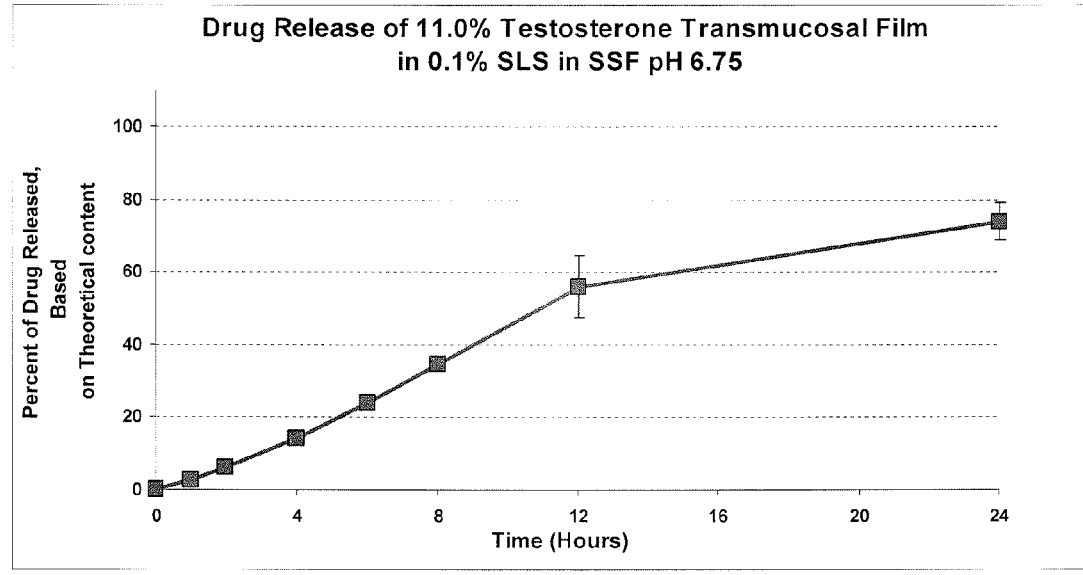
FIGS. 4a and 4b depict release profiles for various different extended release HME compositions made according to the invention.
Figure 4B:
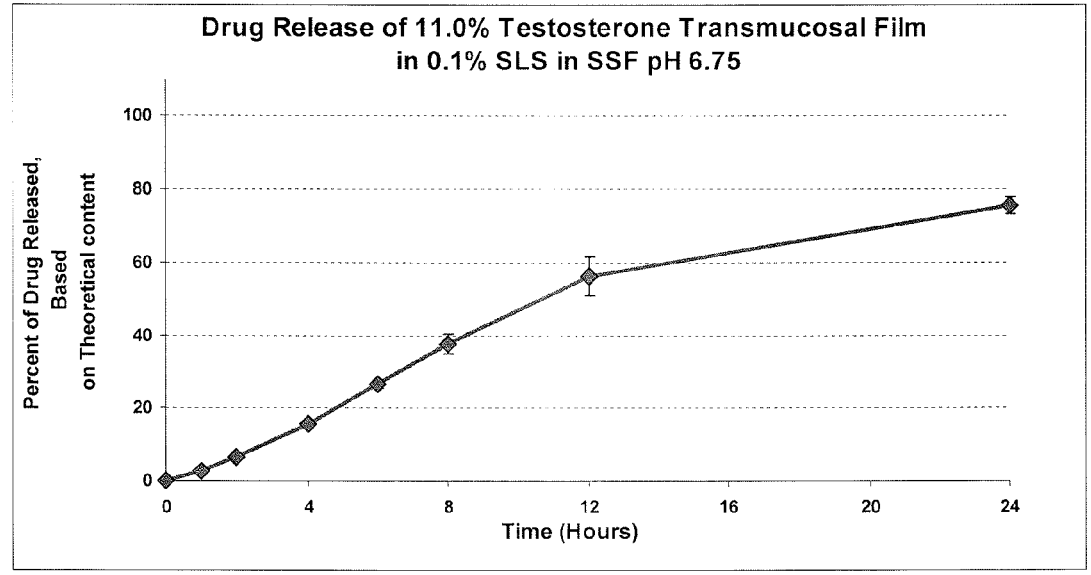

Formulations providing an extended release of drug can be made. Two formulations were prepared using higher Carbopol loads in which the target film thickness was 1.50 mm. These formulations were prepared by the hydroalcoholic wet granulation technique in which the Vitamin E and Vitamin E Succinate were emulsified with the Poloxamer. The in vitro dissolution profiles are presented in FIGS. 4a and 4b. The formulations differed in the amount of CARBOPOL polymer present: 12.5% (FIG. 4a); 15% (FIG. 4b). It can be concluded that increasing the dose thickness (increasing the thickness of the drug-containing composition or layer) and increasing the Carbopol content in the formulation retards the in vitro dissolution rate. The thickness of the reservoir layer can range from about 0.01 to about 20 mm or otherwise be manufactured in any size adapted for a particular purpose.

The effectiveness of an acidic component as a neutralizer of the alkaline thermoplastic matrix may vary. As a result, its performance in stabilization of an alkaline labile drug should be evaluated by preparing hot-melt extruded compositions, using a procedure described herein, containing varying amounts of the acidic component, and similar amounts of all other components. The HME compositions are then analyzed, such as by HPLC, to determine the differences in their purity profiles. The HME composition containing the lowest comparative amount of impurities is the better composition. In a similar manner, various HME compositions containing the same amount of different acidic components can be prepared and analyzed as described herein. The acidic component resulting in a HME composition having the least amount of impurities is the better acidic component. For example, POLYOX (PEO) polymers contain residual calcium salts from the catalyst during synthesis. A series of experiments was conducted using hydrochloric acid and phosphoric acid to neutralize these alkaline materials. The acidic component was added in liquid form to the granulation mass or the granulation liquid medium. A formulation as described herein was prepared but was wet granulated with either 50 mM hydrochloric Acid or 100 mM Phosphoric Acid. Twenty doses were sampled from each lot at the beginning, middle and end of the extrusion run. Composites of 10 doses were analyzed for impurities in duplicate. Major impurities were not identified in the samples neutralized with hydrochloric acid. Small quantities of the 6B-Hydroxy-testosterone were detected in the phosphoric acid sample. It was determined that HCl provided better stabilization of testosterone than does $H_3PO_4$ even though both were acceptable under the evaluation criteria.

The total acidic component is present in an amount sufficient to neutralize alkaline species present in the matrix. In other words, the acidic component is added in an amount sufficient to achieve a pH within the desired range (e.g., 7 or less or less than the pH which results in degradation of the alkaline labile species). In one embodiment, the total molar concentration of acidic component (or of total acidic groups) equals or exceeds the molar concentration of total alkaline groups present in the excipient composition. An acidic component can have 1, 2 or more moles of acidic groups per mole of acidic component.

Optionally, no wet granulation is required. In this embodiment, all materials to be added to a formulation are blended and then hot-melt extruded. This process, however, is only suitable when water soluble acidic components are used, as non-water soluble acidic components, such as CARBOPOL®, do not stabilize the film as well in this type of process. This because CARBOPOL® requires water for hydration in order to exert its acidic property. One way to overcome this disadvantage is to wet the non-water soluble acidic component prior to granulation with the bioadhesive alkaline thermoplastic polymer and extending the granulation time sufficiently to permit interaction of the non-water soluble acidic component with the bioadhesive alkaline thermoplastic polymer to form a neutral or moderately acidic excipient mixture.

As used herein, the term "acidic component" or "acidifying agent" means one or more acidic polymers (e.g. Carbopol®, Polycarbophil, polyacrylic acid), one or more inorganic acids (e.g. a mineral acid, (phosphoric acid, boric acid, hydrochloric acid, nitric acid, sulfuric acid, hydrobromic acid), one or more organic acids (non-polymeric carboxylic acid such as acetic acid, citric acid, tartaric acid, turmeric acid, succinic acid, amino acid, alpha-hydroxyl acid, ascorbic or adipic acid), or a combination thereof. An acidic component also includes the salt form or buffer of an acid, wherein the salt has solution pH of less than 7 or less than 6 when dissolved in water. The above-listed acidic components are merely illustrative and non-limiting. Any acidic component having a pKa of less than 7 or less than 6 would be suitable for use in the present invention. Specific embodiments include those wherein the acidic component is selected from the group consisting of: hydrochloric acid, phosphoric acid, citric acid and a combination thereof.

An acidic component can be a combination of an acidic polymer and an organic acid, an acidic polymer and an inorganic acid, or an inorganic acid and an organic acid. An acidic component may also be a combination or two or more acidic polymers, two or more inorganic acids, or two or more organic acids.

Some lots incorporated citric acid as a secondary acidifier without an antioxidant. The blend was wet granulated with water at 5% and extruded using the Randcastle at 135° C.

| Lot No./ Temp. (° C.) | Total Unknown Impurities (%)* | 6B-Hydroxy-testosterone (%) | 4-Androsten-16-alpha-ol-3,17-dione (%) | Epi-Testosterone[b] (%) |
|---|---|---|---|---|
| No. 56 135° C. | 2.90 | ND | ND | ND |
| No. 61 135° C. | 0.95 | 0.1 | ND | ND |

*Degradants were not detected in the samples, although a peak (likely citric acid) eluted between the major impurities.

The solid dosage formulations of the invention can assume any shape or form known in the art of pharmaceutical sciences. The dosage form can be a sphere, tablet, bar, plate, paraboloid of revolution, ellipsoid of revolution or other one known to those of ordinary skill in the art. The solid dosage form can also include surface markings, cuttings, grooves, letters and/or numerals for the purposes of decoration, identification and/or other purposes.

The matrix and/or the additional functional excipients may be formulated so as to provide a predetermined approximate release profile under predetermined conditions. The drug can be released according to an immediate, rapid, sustained, controlled, slow, or extended, and optionally delayed, or targeted drug release profile.

The pharmaceutical composition may deliver one or more active agents in an extended release manner, and mechanisms employed for such delivery can include active agent release that is pH-dependent or pH-independent; diffusion or dissolution controlled; erosion controlled; pseudo-zero order (approximates zero-order release), zero-order, pseudo-first order (approximates first-order release), or first-order; or slow, delayed, timed or sustained release or otherwise controlled release. The release profile for the active agent can also be sigmoidal in shape, wherein the release profile comprises an initial slow release rate, followed by a middle faster release rate and a final slow release rate of active agent.

As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. An extended release tablet generally effects at least a two-fold reduction in dosing frequency as compared to the drug presented in a conventional dosage form (e.g., a solution or rapid releasing conventional solid dosage forms).

By "controlled release" is meant a release of an active agent to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered. The term "controlled release", as regards to drug release, includes the terms "extended release", "prolonged release", "sustained release", or "slow release", as these terms are used in the pharmaceutical sciences. A controlled release can begin within a few minutes after administration or after expiration of a delay period (lag time) after administration.

A slow release dosage form is one that provides a slow rate of release of drug so that drug is released slowly and approximately continuously over a period of 3 hr, 6 hr, 12 hr, 18 hr, a day, 2 or more days, a week, or 2 or more weeks, for example.

A timed release dosage form is one that begins to release drug after a predetermined period of time as measured from the moment of initial exposure to the environment of use.

A targeted release dosage form generally refers to a dosage form that is designed to deliver drug to a particular portion of the dermis or mucosa of a subject.

By "delayed release" is meant that initial release of drug occurs after expiration of an approximate delay (or lag) period. For example, if release of drug from an extended release composition is delayed two hours, then release of drug from begins at about two hours after administration of the composition, or dosage form, to a subject. In general, a delayed release is opposite an immediate release, wherein release of drug begins after no more than a few minutes after administration. Accordingly, the drug release profile from a particular composition can be a delayed-extended release. A "delayed-extended" release profile is one wherein extended release of drug begins after expiration of an initial delay period.

A pseudo-first order release profile is one that approximates a first order release profile. A first order release profile characterizes the release profile of a dosage form that releases a constant percentage of an initial drug charge per unit time.

A pseudo-zero order release profile is one that approximates a zero-order release profile. A zero-order release profile characterizes the release profile of a dosage form that releases a constant amount of drug per unit time.

Figure 2:
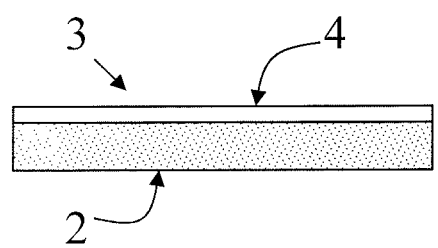
FIG. 2 depicts a cross-sectional front elevation of an exemplary embodiment of a bi-layered hot-melt extruded composition according the invention.

FIG. 2 depicts a conceptual cross-sectional front elevation of an exemplary bi-layered hot-melt extruded composition (3) (a laminate) comprising a drug reservoir layer (2) and a backing layer (4). The drug reservoir is a bioadhesive layer comprising an alkaline labile drug, acidic component, and bioadhesive alkaline thermoplastic polymer. The backing layer is non-bioadhesive and generally more hydrophobic than the reservoir layer.

The hydrophobic composition of the backing layer generally comprises a hydrophobic non-bioadhesive thermoplastic matrix. Suitable materials that can be used in preparing the matrix of the backing layer include, by way of example and without limitation, EUDRAGIT, ethylcellulose, polyethylene, cellulose acetate butyrate, cellulose acetate phthalate, wax, polyvinyl alcohol, polyvinyl acetate phthalate, polyester, shellac, other materials recognized in the chemical arts as having similar physical properties, or a combination thereof. The backing layer can be extruded as described herein or it can be a prefabricated layer that is subsequently laminated to the reservoir layer. Alternatively, the backing layer can be cast onto the drug-containing layer. In one embodiment, the backing layer is impermeable to aqueous medium and drug. Non-limiting exemplary materials suitable for this type of backing layer include ethylcellulose, EUDRAGIT RS, wax, other materials recognized in the chemical arts as having similar physical properties, or a combination thereof. In another embodiment, it is semipermeable, meaning it is impermeable to drug and permeable to aqueous medium. Non-limiting exemplary materials suitable for this type of backing layer include PEO and ethylcellulose, PEO and EUDRAGIT RS, cellulose acetate and its derivatives, other materials recognized in the chemical arts as having similar physical properties, or a combination thereof. In still another embodiment, it is permeable to aqueous medium and drug. Non-limiting exemplary materials suitable for this type of backing layer include PEO and EUGRAGIT E, other materials recognized in the chemical arts as having similar physical properties, or a combination thereof.

The backing layer is typically inert, meaning it does not contain a therapeutically active agent. However, the backing layer can optionally include a therapeutically active agent, and its active agent can be the same as or different than the one in the reservoir layer.

An exemplary backing layer was made according to the examples below. In one embodiment, the hydrophobic composition of the backing layer is extruded separately from the hydrophilic composition of the reservoir layer. In another embodiment, the hydrophobic composition of the backing layer is coextruded with the hydrophilic composition of the reservoir layer. In one embodiment, the backing layer and reservoir layers are extruded and shortly thereafter heat-laminated, solvent-laminated, or adhesive-laminated together during manufacture. In another embodiment, the backing layer and the reservoir layer are extruded separately and subsequently heat-laminated, solvent-laminated or adhesive-laminated together. In another embodiment, one layer is extruded onto the other layer which has been preformed, such as by extrusion or casting.

The step of heat-catalyzed lamination is conducted by passing the backing layer and reservoir layer in contact with each other simultaneously through a laminator that applies pressure and optionally heat to the opposing layers. If the layers are sufficiently hot prior to lamination, they need not be heated again when placed in the laminator. If the layers are not sufficiently hot prior to lamination to permit suitable lamination, then they are heated just prior to and/or during lamination. The heat source can be located within or external to the laminator. The layers will generally be heated to about 100-170° C. or at least about 60° C. prior to and/or during lamination. The temperature for lamination will be below the temperature at which a layer degrades.

Lamination can also be achieved without heat by applying a fine mist of water or other suitable solvent or plasticizer two one or both of the opposing layers immediately prior to combining under pressure. This solvent lamination process is suitable when the reservoir layer and the backing layer each comprise a solvent-activated or plasticizer-activated adhesive material such as PEO.

The laminator can be a set of opposing rollers driven by one or two motors. The laminator will apply pressure to both layers during the lamination step. The contact pressure will generally be at least 40 pounds per linear inch or in the range of about 40-600 pounds per linear inch. The laminator rollers will be sufficiently rigid to withstand the forces exerted. The rollers may be hollow and internally baffled to allow for the use of a heat transfer fluid. The rollers may be comprised of a multiple metals and/or alloys providing suitable hardness and may contain suitable coatings to provide adequate release of the heated polymer. Suitable coatings for the rollers include, for example, Teflon®, Titanium Nitride, Chrome, and other material(s) used in the polymer industry for coating of heat laminators.

When the reservoir layer is adhesive-laminated to the backing layer, the adhesive is a material known in the field of polymers as suitable to adhering the two layers together. The specific adhesive will vary according to the chemical composition, chemical properties, and physical properties of the reservoir layer and the backing layer. A non-limiting exemplary adhesive comprises KLUCEL and EUDRAGIT E100. For example, a bioadhesive reservoir layer comprising a hydrophilic HME matrix can be adhered to a non-bioadhesive backing layer comprising a hydrophobic HME matrix by applying an adhesive material at the interface between the two layers and subsequently pressing the two layers together. Weight or pressure can be applied to the layers optionally followed by drying to remove solvent, if present, from the adhesive.

Since the backing layer can be intimate contact with the reservoir layer, its pH might impact the stability of the drug in the reservoir layer. Studies to investigate the pH (when placed in solution) of the backing layer were conducted to eliminate the potential for drug degradation at the interface between the backing layer and the reservoir layer in a laminate composition. Such degradation may occur during heat-catalyzed lamination or during storage of the laminate. The pH of the backing layer (made according to one of the examples below) was determined to be 9.0 after dispersing 2 grams in 100 mL of purified water. The pH of the suspension was determined after aliquots of citric acid monohydrate were added. Addition of 10 mg of citric acid reduced the suspension pH to 4.6 and addition of 50 mg reduced the suspension pH to 3.4. A backing film formulation was prepared containing 1.0% citric acid. The citric acid monohydrate was dissolved in water (5% based on solids) and wet granulated with the PolyOx polymers. The remaining materials were blended under high shear followed by granulation with dibutyl sebacate. The results indicate decreased degradation of drug in the reservoir layer when the backing layer included an acidic component in an amount sufficient to render the solution pH of the backing film less than about 7 or less than the pH at which the alkaline labile drug degrades.

The ratio of the thickness of the reservoir layer to the thickness of the backing layer can be varied as needed depending upon the performance desired for the laminate. In one embodiment, the ratio ranges from about 0.1:1 to about 5:1 or about 1:1 to 4:1.

When the backing layer and reservoir layer are laminated together by heat-catalyzed lamination, they will preferably have at least one polymer in common. For example, if the reservoir layer contains PEO, then the backing layer could contain PEO.

Generally, the reservoir layer and the backing layer possess melt flow indices that are not too dissimilar if the layers are to be laminated by heat-catalyzed lamination in the absence of an adhesive between the layers. This means their melt flow indices will fall within individual predefined ranges and that those ranges overlap at least to some predefined extent. For example, the melt flow index of the reservoir layer can be within no more than 75% or within no more than 50% of the melt flow index of the backing layer. As used herein, the term melt flow index is taken to mean the amount, in grams, of a resin which can be forced through a plastometer or rheometer (as defined in ASTM D1238) in ten minutes at a given temperature and force.

Figure 3:
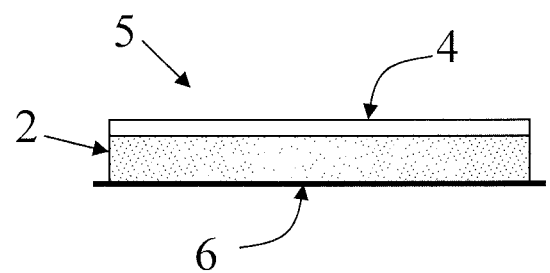
FIG. 3 depicts a cross-sectional front elevation of an exemplary embodiment of a tri-layered hot-melt extruded composition according the invention.

FIG. 3 depicts a conceptual cross-sectional front elevation of an exemplary tri-layered hot-melt extruded composition (5) comprising a drug reservoir layer (2), a backing layer (4) and a release liner layer (6). The drug reservoir is a bioadhesive layer comprising an alkaline labile drug, acidic component, and bioadhesive alkaline thermoplastic polymer. The backing layer is non-bioadhesive and generally more hydrophobic than the reservoir layer.

The release liner layer temporarily adheres to the bioadhesive layer during storage of the HME composition, and it is removable by hand before administration of the HME composition to a subject. The release layer may or may not be coextruded with the other two layers.

Any release layer that can temporarily adhere to the reservoir layer will be suitable for use according to the invention. Exemplary non-limiting suitable release layers obtainable from commercial sources include DOW SARANEX™, DOW BLF, 3M CoTran and SCOTCHPAK, Delstar Stratex and Delnet.

The release layer is attached to the face of the reservoir layer that is opposite the backing layer such that the release layer and backing layer oppose one another. In other words, the reservoir layer is between the release layer and the backing layer. The contact surface area of the release layer can be the same size as or bigger than the corresponding contact surface of the reservoir layer.

The matrix of the invention may also contain various functional excipients, such as: hydrophilic polymer, antioxidant, super-disintegrant, surfactant including amphiphillic molecules, wetting agent, stabilizing agent, retardant, thermal lubricant, colorant, solubilizer, chelating agent, similar functional excipient, or combination thereof, and plasticizers including citrate esters, polyethylene glycols, PG, triacetin, diethylphthalate, castor oil, and others known to those or ordinary skill in the art. Extruded material may also include an acidifying agent, adsorbent, alkalizing agent, buffering agent, colorant, flavorant, sweetening agent, diluent, opaquant, complexing agent, fragrance, preservative or a combination thereof.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

A buffering agent is used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

Exemplary chelating agents include EDTA, polycarboxylic acids, polyamines, derivatives thereof, and others known to those of ordinary skill in the art.

Exemplary hydrophilic polymers which can be a primary or secondary polymeric carrier that can be included in the composition include poly(vinyl alcohol) (PVA), polyethylene-polypropylene glycol (e.g. POLOXAMER™), carbomer, polycarbophil, or chitosan. The "hydrophilic polymers" of the present invention include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan, and povidone. "Hydrophilic polymers" also include polyethylene oxide, sodium carboxymethycellulose, hydroxyethyl methyl cellulose, hydroxymethyl cellulose, carboxypolymethylene, polyethylene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

Exemplary hydrophobic polymers include alkylcelluloses, ethyl cellulose, Eudragit RS, waxes, polyesters, combinations thereof, and others known to those of ordinary skill in the art.

Thermal lubricants include glyceryl monostearate, vitamin E succinate, glycerol monooleate, combinations thereof, and others known to those of ordinary skill in the art.

Solubilizers include cyclodextrins, povidone, combinations thereof, and others known to those of ordinary skill in the art.

As used herein, the term "antioxidant" is intended to mean an agent that inhibits oxidation and thus is used to prevent the deterioration of preparations by oxidation due to the presence of oxygen free radicals or free metals in the composition. Such compounds include, by way of example and without limitation, ascorbic acid, ascorbyl palmitate, butylated hydroxyanisole, butylated hydroxytoluene, hypophophorous acid, monothioglycerol, sodium ascorbate, sodium formaldehyde sulfoxylate and sodium metabisulfite and others known to those of ordinary skill in the art. Other suitable antioxidants include, for example, vitamin C, BHT, BHA, sodium bisulfate, vitamin E and its derivatives, propyl gallate or a sulfite derivative.

As used herein, the term "disintegrant" is intended to mean a compound used in solid dosage forms to promote the disruption of a solid mass (layer) into smaller particles that are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g., Avicel™) carboxymethylcellulose calcium, croscarmellose sodium, alginic acid, sodium alginate, cellulose polyacrilin potassium (e.g., Amberlite™), alginates, sodium starch glycolate, gums, agar, guar, locust bean, karaya, pectin, tragacanth, crospovidone and other materials known to one of ordinary skill in the art. A superdisintegrant is a rapidly acting disintegrant. Exemplary superdisintegrants include crospovidone and low substituted HPC.

Suitable surfactants include Polysorbate 80, sorbitan monooleate, sodium lauryl sulfate or others. Soaps and synthetic detergents may be employed as surfactants. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene)copolymers; and amphoteric detergents, for example, alkyl β-aminopropionates and 2-alkylimidazoline quaternary ammonium salts; and mixtures thereof.

Wetting agent is an agent that decreases the surface tension of a liquid. Wetting agents would include alcohols, glycerin, proteins, peptides water miscible solvents such as glycols, hydrophilic polymers Polysorbate 80, sorbitan monooleate, sodium lauryl sulfate, fatty acid alkali metal, ammonium, and triethanolamine salts, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene)copolymers; and amphoteric detergents, for example, alkyl β-aminopropionates and 2-alkylimidazoline quaternary ammonium salts; and mixtures thereof.

Retardants are agents that are insoluble or slightly soluble polymers with a Tg above 45° C., more preferably above 50° C. before being plasticized by other agents in the formulation including other polymers and other excipients needed for processing. The excipients include waxes, acrylics, cellulosics, lipids, proteins, glycols, and the like.

A desiccant can be used to aid in storing a formulation according to the invention. Suitable desiccants include sodium sulfate, calcium sulfate, magnesium sulfate, sodium hydroxide, sodium bicarbonate, clay, vermiculite, paper, activated alumina, zeolite, calcium chloride, molecular sieve, or anhydrous chemicals. In some cases a dessicant is needed if the matrix materials or the drug are hygroscopic since moisture may affect the stability of the HME composition and/or drug therein.

As used herein, the term "opaquant" is intended to mean a compound used to render a composition opaque. It may be used alone or in combination with a colorant. Such compounds include, by way of example and without limitation, titanium dioxide and other materials known to one of ordinary skill in the art.

Some of the materials listed herein may be too brittle or may have Tg values that are generally too high rendering them too difficult to extrude. The glass transition temperature is reduced upon the addition of a plasticizer. As used herein, the glass transition temperature is taken to mean the temperature at which a solid material softens or melts (or the glass transition temperature (Tg) is the temperature at which a polymer changes during the heat cycle from a brittle substance (glass) to a rubbery mass). Such materials can be combined with one or more plasticizers to render them thermoformable. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the film of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

Preservatives include compounds used to prevent the growth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leaf oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The HME composition of the invention will include at least one active agent when included in a dosage form. Generally an effective amount of active agent is included. By the term "effective amount", it is understood that, with respect to, for example, pharmaceuticals, a therapeutically effective amount is contemplated. A therapeutically effective amount is the amount or quantity of drug that is sufficient to elicit the required or desired therapeutic response, or in other words, the amount that is sufficient to elicit an appreciable biological response when administered to a patient.

The active agent can be present in its free acid, free base or pharmaceutically acceptable salt form. As used herein, "pharmaceutically acceptable salts" refer to derivatives of the disclosed compounds wherein the active agent is modified by making acid or base salts thereof. Examples of pharmaceutically acceptable salts include, but are not limited to, mineral or organic acid salts of the drug. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and other known to those of ordinary skill in the pharmaceutical sciences. Lists of suitable salts are found in texts such as *Remington's Pharmaceutical Sciences,* 18th Ed. (Alfonso R. Gennaro, ed.; Mack Publishing Company, Easton, Pa., 1990); *Remington: the Science and Practice of Pharmacy* 19$^{th}$ Ed. (Lippincott, Williams & Wilkins, 1995); *Handbook of Pharmaceutical Excipients,* 3$^{rd}$ Ed. (Arthur H. Kibbe, ed.; Amer. Pharmaceutical Assoc., 1999); the *Pharmaceutical Codex: Principles and Practice of Pharmaceutics* 12$^{th}$ Ed. (Walter Lund ed.; Pharmaceutical Press, London, 1994); The United States Pharmacopeia: The National Formulary (United States Pharmacopeial Convention); and *Goodman and Gilman's: the Pharmacological Basis of Therapeutics* (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The alkaline-labile drug can be included in the HME composition in crystalline or amorphous form. It can be a salt, free-base, or free-acid. It can be non-ionic, polar, apolar, cationic, or anionic. It can be present in hydrous or anhydrous form. The active agent can be present in its diastereomeric, isomeric, enantiomerically pure, racemic, hydrate, chelate, derivative, analog, or other common form.

Active agents include compounds (therapeutic compounds) for pharmaceutical use, such as human or veterinary use.

As used herein, the terms "therapeutic compound", "therapeutic agent", "active agent" and "drug" are used interchangeably, unless otherwise specified. The process of the invention can be used to prepare composition and dosage forms comprising essentially any one or more active agents. Active agents include physiological substances or pharmacological active substances that produce a systemic or localized effect or effects on animals and human beings.

A specific aspect of the invention includes one or more alkaline labile active agents. An alkaline labile active agent is one that degrades under alkaline conditions during processing and/or storage. Alkaline is defined as a pH of greater than 7. For example, when a material being tested is dissolved or dispersed in water, the liquid (water) will have a pH of greater than 7. An alkaline polymer is a polymer that forms a solution having a pH greater than 7 when the polymer is placed, dissolved and/or dispersed in water. Exemplary alkaline labile active agents include one or more functional groups selected from the group consisting of an ester, amide, urea, acetal, ketal, carbamate, carbonate, lactone, lactam, halide, nitrate, phosphate, sulfate, sulfonate, phosphonate, imidate, imine, sulfide, hydroxide-reactive (hydroxide-unstable) functional group and amine reactive (amine unstable) functional group. By "hydroxide-reactive" or "hydroxide unstable" functional group is meant a functional group that reacts with a hydroxide moiety when placed in an alkaline medium. By "amine-reactive" or "amine unstable" functional group is meant a functional group that reacts with a primary, secondary or tertiary amine moiety when placed in an alkaline medium.

Particular alkaline labile drugs include, by way of example and without limitation, testosterone, oxybutynin, morphine, fentanyl, aspirin, lansoprazole, omeprazole, pantoprazole, rabeprazole, Naltrexone, benzocaine, penicillin G, noradrenaline, isoprenaline, thiamine and atracurium.

Even though the invention is particularly suited for alkaline labile drugs, drugs that are stable under alkaline conditions can also be employed in the process and HME composition of the invention. Active agents include compounds (therapeutic compounds) for pharmaceutical use, such as human or veterinary use. The active agent can be present in its neutral, ionic, salt, basic, acidic, natural, synthetic, diastereomeric, isomeric, enantiomerically pure, racemic, hydrate, chelate, derivative, analog, or other common form.

Further therapeutic compounds which can be formulated into the present composition also include an antibacterial substance, antihistamine (histamine receptor inhibitor), decongestant, anti-inflammatory agent, antiparasitic agent, antiviral agent, local anesthetic, antifungal agent, amoebicidal agent, trichomonocidal agent, analgesic agent, antiarthritic agent, antiasthmatic agent, anticoagulant agent, anticonvulsant agent, antidepressant agent, antidiabetic agent, antineoplastic agent, antipsychotic agent, neuroleptic agent, antihypertensive agent, muscle relaxant, depressant agent, hypnotic agent, sedative agent, psychic energizer, tranquilizer, antiparkinson agent, muscle contractant, anti-microbial agent, antimalarial agent, hormonal agent, contraceptive agent, sympathomimetic agent, diuretic agent, hypoglycemic agent, ophthalmic agent, anti-hypercholesterolemia agent, anti-hypocholesterolemia agent, electrolyte, diagnostic agent, cardiovascular drug, vitamin, nutrient, nutritional agent, hematological agent, endocrine agent, metabolic agent, renal agent, genitourinary agent, respiratory agent, central nervous system agent, gastrointestinal agent, anti-infective agent, biologic agent, immunological agent, dermatological agent, ophthalmic agent, and other type of therapeutic compound known to those of ordinary skill in the pharmaceutical sciences, and combinations thereof.

Exemplary nutrients and nutritional agents include as minerals, trace elements, amino acids, lipotropic agents, enzymes and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes. Exemplary cardiovascular agents include nootropic agents, antiarrhythmic agents, calcium channel blocking agents, vasodilators, antiadrenergics/sympatholytics, renin angiotensin system antagonists, antihypertensive combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, nasal decongestants, respiratory enzymes, lung surfactants, antihistamines, nonnarcotic antitussives, and expectorants. Exemplary central nervous system agents include CNS stimulants, narcotic agonist analgesics, narcotic agonist-antagonist analgesics, central analgesics, acetaminophen, salicylates, nonnarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including H pylori agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, esomeprazole, famotidine, lansoprazole, omeprazole, pantoprazole, rabeprazole, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, such as amoxicilin, cephalosporins and related antibiotics, carbapenem, monobactams, chloramphenicol, quinolones, fluoroquinolones, tetracyclines, macrolides, such as azithromycin, clarithromycin, and the like, spectinomycin, streptogramins, vancomycin, oxalodinones, lincosamides, oral and parenteral aminoglycosides, colistimethate sodium, polymyxin B sulfate, bacitracin, metronidazole, sulfonamides, nitrofurans, methenamines, folate antagonists, antifungal agents, such as fluconazole, voriconazole, and the like, antimalarial preparations, antituberculosis agents, amebicides, antiviral agents, antiretroviral agents, leprostatics, antiprotozoals, anthelmintics, and CDC anti-infective agents. Exemplary biologic and immunological agents including immune globulins, monoclonal antibody agents, antivenins, agents for active immunization, allergenic extracts, immunologic agents, and antirheumatic agents. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, DNA topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

Representative antibacterial substances are beta-lactam antibiotics, tetracyclines, chloramphenicol, neomycin, gramicidin, bacitracin, sulfonamides, aminoglycoside antibiotics, tobramycin, nitrofurazone, nalidixic acid, penicillin, tetracycline, oxytetracycline, chlorotetracycline, erythromycin, cephalosporins and analogs and the antimicrobial combination of fludalanine/pentizidone. Other representative antibacterial agents include of the poorly water-soluble pyridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof.

Representative antiparasitic compounds are ivermectin, bephenium, hydroxynaphthoate, praziquantel, nifurtimox, benznidasol, dichlorophen and dapsone. Representative antimalarial compounds are 4-aminoquinolines, 8-aminoquinolines and pyrimethamine.

Representative antiviral compounds are protease inhibitors, neuramidinase inhibitors, commercially available compounds, acyclovir and interferon.

Representative anti-inflammatory drugs include specific or selective COX-2 receptor inhibitors, rofecoxib, celecoxib, etodolac, flurbiprofen, ibuprofen, ketoprofen, ketorolac, nabumetone, piroxicam, suprofen, tolmetin, zileuton, steroids, cyclooxygenase inhibitors, cortisone, hydrocortisone, betamethasone, dexamethasone, fluocortolone, prednisolone, phenylbutazone, triamcinolone, sulindac, indomethacin, salicylamide, naproxen, colchicine, fenoprofen, diclofenac, indoprofen, dexamethasone, allopurinol, oxyphenbutazone, probenecid and sodium salicylamide.

Representative analgesic drugs are diflunisal, aspirin, ibuprofen, profen-type compounds, morphine, codeine, levorphanol, hydromorphone, oxymorphone, oxycodone, hydrocodone, naloxene, levallorphan, etorphine, fentanyl, bremazocine, meperidine, nalorphine, tramadol, and acetaminophen.

Representative antihistamines and decongestants are acrivastine, astemizole, norastemizol, brompheniramine, cetirizine, clemastine, diphenhydramine, ebastine, famotidine, fexofenadine, meclizine, nizatidine, perilamine, promethazine, ranitidine, terfenadine, chlorpheniramine, cimetidine, tetrahydrozoline, tripolidine, loratadine, desloratadine, antazoline, and pseudoephedrine.

Representative antiasthma drugs are theophylline, ephedrine, beclomethasone dipropionate and epinephrine.

Representative anticoagulants are heparin, bishydroxycoumarin, and warfarin.

Representative psychic energizers are isocoboxazid, nialamide, phenelzine, imipramine, tranycypromine, and parglyene.

Representative anticonvulsants are clonazepam, phenobarbital, mephobarbital, primidone, enitabas, diphenylhydantion, ethltion, pheneturide, ethosuximide, diazepam, phenytoin carbamazepine, lamotrigine, lorazepam, levetiracetam, oxcarbazepine, topiramate, valproic acid, chlorazepate, gabapentin, felbamate, tiagabine and zonisamide.

Representative antidepressants are amitriptyline, chlordiazepoxide perphenazine, protriptyline, imipramine, doxepin, venlafaxine, o-desmethyl venlafaxine, citalopram, escitalopram, bupropion, clomipramine, desipramine, nefazodone, fluoxetine, fluvoxamine, maprotiline, mirtazapine, nortriptyline, paroxetine, phenelzine, tranylcypromine, sertraline, trazodone, trimipramine, and amoxapine.

Representative antidiabetics are sulphonylureas, such as tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones (glitazones), such as rosiglitazone, pioglitazone, and troglitazone; biguanidines, such as metformin; and other antidiabetic agents, such as nateglinide, repaglinide, insulin, somatostatin and its analogs, chlorpropamide, isophane insulin, protamine zinc insulin suspension, globin zinc insulin, and extended insulin zinc suspension.

Representative antineoplastics are chlorambucil, cyclophosphamide, triethylenemelamine, thiotepa, hexamethylmelamine, busulfan, carmustine, lomustine, dacarbazine, arabinoside cytosine, mercaptopurine, azathiprine, vincristine, vinblastine, taxol, etoposide, actinomycin D, daunorubicin, doxorubicin, bleomycin, mitomycin; cisplatin; hydroxyurea, procarbazine, aminoglutethimide, tamoxifen, adriamycin, fluorouracil, methotrexate, mechlorethamine, uracil mustard, 5-fluorouracil, 6-6-thioguanine and procarbazine asparaginase.

Representative steroidal drugs are prednisone, prednisolone, cortisone, cortisol and triamcinolone; androgenic steroids such as methyltesterone, testosterone, and fluoxmesterone; estrogenic steroids such as 17β-estradiol, α-estradiol, estriol, α-estradiol 3 benzoate, and 17-ethynylestradiol-3-methyl ether; progestational steriods such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9β,10α-pregna-4,6-diene-3,20-dione.

Representative estrogen antagonist-agonist drugs are clomiphene citrate and raloxifene HCl.

Representative antipsychotics are prochlorperazine, lithium carbonate, lithium citrate, thioridazine, molindone, fluphenazine, trifluoperazine, perphenazine, amitriptyline, trifluopromazine, chlorpromazine, clozapine, haloperidol, loxapine, mesoridazine, olanzapine, quetiapine, ziprasidone, risperidone, pimozide, mesoridazine besylate, chlorprothixene, and thiothixene.

Representative hypnotics and sedatives are pentobarbital sodium, phenobarbital, secobarbital, thiopental, heterocyclic hypnotics, dioxopiperidines, imidazopyridines, such as zolpidem tartrate, glutarimides, diethylisovaleramide, α-bromoisovaleryl urea, urethanes, disulfanes.

Representative antihypertensives are nifedipine, verapamil, diltiazem, felodipine, amlodipine, isradipine, nicardipine, nisoldipine, nimodipine, bepridil, enalapril, captopril, lisinopril, benazepril, enalaprilat, espirapril, fosinopril, moexipril, quinapril, ramipril, perindopril, trandolapril, furosemide, bumetanide, ethacrynic acid, torsemide, muzolimide, azosemide, piretanide, tripamide, hydrochlorothiazide, chlorthalidone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide, benzothiazide, spironolactone, methyldopa, hydralazine, clonidine, chlorothiazide, deserpidine, timolol, propranolol, metoprolol, pindolol, acebutolol, prazosin hydrochloride, methyl dopa (L-β-3,4-dihydroxyphenylalanine), pivaloyloxyethyl ester of α-methyldopa hydrochloride dihydrate, candesartan cilexetil, eprosartan mesylate, losartan potassium, olmersartan medoxomil, telmisartan, valsartan, and reserpine.

Representative anti-incontinence agents include oxybutynin.

Representative tranquilizers are chloropromazine, promazine, fluphenazine, reserpine, deserpidine, meprobamate, and benezodiazepines (anxyiolitic, sedatives, and hypnotics)

such as alprazolam, chlordiazepoxide, diazepam, lorazepam, oxazepam, temazepam, and triazolam.

Representative anti-spasmodics and muscle contractants are atropine, scopolamine, methscopolamine, oxyphenonium, papaverine, and prostaglandins such as $PGE_1$ $PGE_2$ $PGF_{1\alpha}$ $PGF_{2\alpha}$ and PGA.

Representative local anesthetics are benzocaine, procaine, lidocaine, maepaine, piperocaine, tetracaine and dibucaine.

Representative muscle relaxants are alcuronium, alosetron, aminophylline, baclofen, carisoprodol, chlorphenesin, chlorphenesin carbamate, chlorzoxazone, chlormezanone, dantrolene, decamethonium, dyphylline, eperisione, ethaverine, gallamine triethiodide, hexafluorenium, metaxalone, metocurine iodide, orphenadrine, pancuronium, papaverine, pipecuronium, theophylline, tizanidine, tolperisone, tubocurarine, vecuronium, idrocilamide, ligustilide, cnidilide, senkyunolide, succinylcholine-chloride, danbrolene, cyclobenzaprine, methocarbamol, diazepam, mephenesin, methocarbomal, trihexylphenidyl, pridinol (pridinolum), and biperiden.

Representative anti-Parkinson agents are carbidopa, levodopa, ropinirole, pergolide mesylate, rasagiline, pramipexole, entacapone, benzacide, bromocriptine, selegiline, amantadine, trihexylphenidyl, biperiden, pridinol mesylate, and tolcapone.

Representative anti-Dementia and anti-Alzheimer disease agents are memantine, donepexil, galantamine, rivastigmine, and tacrine Representative sympathomimetic drugs are albuterol, epinephrine, amphetamine ephedrine and norepinephrine.

Representative cardiovascular drugs are procainamide, procainamide hydrochloride, amyl nitrite, nitroglycerin, dipyredamole, sodium nitrate and mannitol nitrate.

Representative diuretics are chlorothiazide, acetazolamide, methazolamide, triamterene, furosemide, indapamide, and flumethiazide.

Representative β-blockers are caravedilol, pindolol, propranolol, practolol, metoprolol, esmolol, oxprenolol, timolol, atenolol, alprenolol, and acebutolol.

Representative phosphodiesterase inhibitors are vardenafil HCl and sildenafil citrate.

Representative antilipemic agents are atorvastatin, cerivastatin, clofibrate, fluvastatin, gemfibrozil, lovastatin, mevinolinic acid, niacin, pravastatin, and simvastatin.

Representative antigout drugs are colchicine, allopurinol, probenecid, sulfinpyrazone, and benzbromadone.

Representative nutritional agents are ascorbic acid, niacin, nicotinamide, folic acid, choline biotin, panthothenic acid, and vitamin $B_{12}$, essential amino acids; essential fats.

Representative electrolytes are calcium gluconate, calcium lactate, potassium chloride, potassium sulfate, sodium chloride, potassium fluoride, ferrous lactate, ferrous gluconate, ferrous sulfate, ferrous fumurate and sodium lactate.

Representative drugs that act on α-adrenergic receptors are clonidine hydrochloride, prazosin, tamsulosin, terazosin, and doxazosin.

Representative mild CNS stimulants are caffeine, modafinil, and methylphenidate hydrochloride.

The formulation of the invention can also be used with unclassified therapeutic agents such as clopidrogel, which is indicated for the reduction of atherosclerotic events (myocardial infarction, stroke, and vascular death) in patients with atherosclerosis documented by recent stroke, recent myocardial infarction, or established peripheral arterial disease.

The active agents (drugs) listed herein should not be considered exhaustive and is merely exemplary of the many embodiments considered within the scope of the invention.

Many other active agents can be administered with the formulation of the present invention. Suitable drugs are selected from the list of drugs included herein as well as from any other drugs accepted by the U.S.F.D.A. or other similarly recognized authority in Canada (Health Canada), Mexico (Mexico Department of Health), Europe (European Medicines Agency (EMEA)), South America (in particular in Argentina (Administracion Nacional de Medicamentos, Alimentos y Tecnologia Médica (ANMAT) and Brazil (Ministério da Saúde)), Australia (Department of Health and Ageing), Africa (in particular in South Africa (Department of Health) and Zimbawe (Ministry of Health and and Child Welfare),) or Asia (in particular Japan (Ministry of Health, Labour and Welfare), Taiwan (Executive Yuans Department of Health), and China (Ministry of Health People's Republic of China)) as being suitable for administration to humans or animals. Preferred embodiments of the invention include those wherein the active substance is pharmacologically or biologically active or wherein the environment of use is the GI tract of a mammal.

The amount of therapeutic compound incorporated in each dosage form will be at least one or more unit doses and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. The appreciable biological response may occur as a result of administration of single or multiple unit doses of an active substance. A dosage form according to the invention that comprises two or more active agents can include subtherapeutic amounts of one or more of those active agents such that an improved, additive or synergistic clinical benefit is provided by the dosage form. By "subtherapeutic amount" is meant an amount less than that typically recognized as being therapeutic on its own in a subject to which the dosage form is administered. Therefore, a dosage form can comprise a subtherapeutic amount of a first drug and a therapeutic amount of a second drug. Alternatively, a dosage form can comprise a subtherapeutic amount of a first drug and a subtherapeutic amount of a second drug.

The term "unit dose" is used herein to mean a dosage form containing a quantity of the therapeutic compound, said quantity being such that one or more predetermined units may be provided as a single therapeutic administration.

The active agent can be present in any particle size suitable for hot-melt extrusion. Fine particle sizes and larger particle sizes can be used. It can be added as a liquid, solid, emulsion, or any other suitable form.

There are several methods well known in the pharmaceutical literature for producing fine drug particles in the micro or nanometer size range. These methods can be divided into three primary categories: (1) mechanical micronization (2) solution based phase separation and (3) rapid freezing techniques. Drug particles made according to any of these techniques will be suitable for use in the present pharmaceutical composition.

Such processes include mechanical milling by ball mill, jet mill, or other similar grinding process; solution based phase separation techniques such as spray drying, emulsification/evaporation, emulsification/solvent extraction, complex coacervation, gas antisolvent precipitation (GAS), precipitation with a compressed antisolvent (PCA), aerosol solvent extraction system (ASES), evaporative precipitation into aqueous solution (EPAS), supercritical antisolvent (SAS), solution-enhanced dispersion by supercritical fluids (SEDS), rapid expansion from supercritical to aqueous solutions (RESAS), pressure induced phase separation (PIPS); or freezing techniques such as spray freezing into liquid (SFL) and ultra rapid freezing (URF). Detailed descriptions of these methods are included in references cited herein, the entire disclosures of which are hereby incorporated by reference.

Mechanical micronization is most commonly done by milling techniques that can produce particles in the range of 1 to 20 microns. The most common processes utilized for this type of mechanical particle size reduction are ball and jet milling.

There are many solution based phase separation processes documented in the pharmaceutical literature for producing micro and nano-sized drug particles. Some of the more commonly known processes are spray drying, emulsification/evaporation, emulsification/solvent extraction, and complex coacervation. Some of the lesser-known processes are, for the sake of brevity, listed below along with their respective illustrating references: a) gas antisolvent precipitation (GAS)—and WO9003782 EPO437451 EPO437451 DK59091; b) precipitation with a compressed antisolvent (PCA)—and U.S. Pat. No. 5,874,029; c) aerosol solvent extraction system (ASES)—; d) evaporative precipitation into aqueous solution (EPAS)—US patent application 20040067251; e) supercritical antisolvent (SAS)—; f) solution-enhanced dispersion by supercritical fluids (SEDS)—; and g) rapid expansion from supercritical to aqueous solutions (RESAS)—.

Freezing techniques for producing micro or nano-sized drug particles are listed below along with their respective illustrating references: a) spray freezing into liquid (SFL)—WO02060411 USPTO App. #2003054042 and 2003024424; and b) ultra rapid freezing (URF).

Drug-containing particles may or may not undergo substantial aggregation or agglomeration during hot-melt extrusion and/or will be disaggregated to essentially primary particles during hot-melt extrusion due to the intense mixing and agitation that occurs during the process. In some cases, the extrudate may need to be processed more than one time through the extruder in order to provide the desired degree of disaggregation. As used herein, the term "disaggregate", as used in reference to the drug-containing particles, means to reduce a loosely bound agglomerate to essentially its primary constituent particles. As used herein, the term "to agglomerate" or "agglomeration", as used in reference to the drug-containing particles means individual particles form a larger particle.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

Preparation of the Excipient Mixture

Method A. Wet Granulation with Water.

A bioadhesive alkaline thermoplastic polymer is wet granulated with water, and an acidic component under high shear until the ingredients were uniformly mixed. One or more other bioadhesive polymers are optionally included in the granulation. One or more other thermoplastic polymers are optionally included in the granulation. One or more other alkaline polymers are optionally included in the granulation. One or more antioxidants are included in the granulation. One or more plasticizers are optionally included in the granulation. One or more excipients are optionally included in the granulation. After granulations, the granulate is optionally dried.

Method B. Wet Granulation with Buffer.

The process of Method A is followed except that a buffer rather than water is used as the liquid medium used for granulation.

Method C. Wet Granulation with Aqueous Organic Solvent.

The process of Method A or Method B is followed except that a water miscible organic solvent is included in the liquid medium used for granulation. The liquid medium can comprise a major portion of water (or buffer) or organic solvent. The liquid medium generally contains at least 5% water (or buffer).

Method D. Wet Granulation with an Aqueous Mineral Acid Solution.

The process of Method A or Method B is followed except that an aqueous solution containing mineral acid is used as the liquid granulation medium.

Method E. Hydroalcoholic Wet Granulation with a Mineral Acid.

The process of Method A or Method B is followed except that a water miscible organic solvent is included in the mineral acid liquid medium for granulation. The liquid medium can comprise a major portion of water, mineral acid or organic solvent. The liquid granulation medium generally contains at least 5% water.

Method F. Wet Granulation with a Mineral Acid in the Presence of an Alkaline Labile Drug.

The process of Method A or Method B is followed except that a mineral acid is used as the liquid granulation medium and the acid labile drug is present during the granulation step.

Method G. Hydroalcoholic Wet Granulation with a Mineral Acid in the Presence of an Alkaline Labile Drug The process of Method A or Method B is followed except that a water miscible organic solvent is included in the mineral acid liquid medium for granulation and the acid labile drug is present during the granulation step. The liquid medium can comprise a major portion of water, mineral acid or organic solvent. The liquid granulation medium generally contains at least 5% water.

Method H. Dry Granulation

A bioadhesive alkaline thermoplastic polymer and an acidic component are dry granulated under high shear until the ingredients were uniformly mixed. One or more other bioadhesive polymers are optionally included in the granulation. One or more other thermoplastic polymers are optionally included in the granulation. One or more other alkaline polymers are optionally included in the granulation. One or more antioxidants are included in the granulation. One or more plasticizers are optionally included in the granulation. One or more excipients are optionally included in the granulation.

EXAMPLE 2

The following process was used to prepare a hot-melt extruded composition according to the invention. The following ingredients in the amounts indicated were used in preparing hot-melt extruded control and sample compositions containing testosterone (Ts) as the active agent.

Method A.

An excipient mixture prepared according to Example 1 is mixed with an alkaline labile drug and blended under high shear to form a uniform blend. The blend is hot-melt extruded using an extruder equipped with a film (sheet) die.

Method B.

Method A is followed with the following exceptions. A Randcastle Taskmaster hot-melt extruder equipped with a 6-inch flat die was operated at 60-90 RPM, 6-9 Drive Amps with an Extrusion Temperature from about 65-135° C. to prepare the composition. All powders were blended in a v-shell blender prior to extrusion. Temperature zones were set as follows: zone 1: 65° C., zone 2: 120° C., zone 3: 125° C., zone 4: 135° C., die temperature 135° C. The powder blend was placed in a feed hopper that is located at the head of a horizontal screw such that the material is starve fed by a mass flow controller operated at 1.5 kg/hr. The residence time of the material in the extruder was approximately three to five minutes. The extrudate was cut into approximately one-foot sections after exiting the die and placed on an aluminum sheets and allowed to cool at ambient conditions. In one embodiment, the granulated wet mass was placed in the feed hopper.

EXAMPLE 3

Method A.

The combined processes of Examples 1 and 2 are used to prepare a hot-melt extruded composition according to the invention. The following ingredients in the amounts indicated were used in preparing hot-melt extruded control and sample compositions containing testosterone (Ts) as the active agent.

| Raw Material | % w/w |
| --- | --- |
| Testosterone, USP | 15.00 |
| Polyethylene Oxide | 64.00 |
| (PolyOx WSR N80, WSR N12K, WSR 301) | |
| Carbopol 974P | 10.00 |
| Vitamin E Succinate | 5.00 |
| Titanium Dioxide | 1.00 |
| Poloxamer 407 | 5.00 |

Testosterone and any other ingredients were added to the wet granulated excipient mixture prepared according to Example 1. The blend was extruded as a monolayer film using a having a barrel temperature of 135° C. The moisture content of the blend prior to extrusion was 3.1%. The HME composition is then analyzed by HPLC according to Example 4 to determine the amount of degradants present.

The PEO can be a single grade of PEO or it can comprise two, three or more different grades of PEO, e.g. PEO Grade 1, PEO Grade 2, PEO Grade 3. The amount of each individual grade can be selected from those amounts disclosed herein.

Method B. Use of two acidic components (acidic organic acid, acidic polymer) and an antioxidant.

| Raw Material | % w/w |
| --- | --- |
| Testosterone, USP | 15.00 |
| Polyethylene Oxide | 64.00 |
| (PolyOx WSR N80, WSR N12K, WSR 301) | |
| Carbopol 974P | 10.00 |
| Citric Acid Monohydrate | 1.00 |
| Butylated Hydroxytoluene | 4.00 |
| Titanium Dioxide | 1.00 |
| Poloxamer 407 | 5.00 |

The procedure of Example 1 was followed except that citric acid was added as a secondary acidifier and butylated hydroxytoluene was added as an antioxidant in place of Vitamin E succinate. As above, the excipient mixture was prepared by wet granulating the PolyOx and Poloxamer with 5% water under high shear. Carbopol was added and blended until uniform.

The amount of each individual grade of PEO can be selected from those amounts disclosed herein.

Method C. Use of Two Acidic Components (Non-Polymeric Organic Acid, Acidic Polymer) without an Antioxidant.

The procedure of Example 1 was followed except that citric acid was added as a secondary acidifier. As above, the lot was prepared by wet granulating the PolyOx and Poloxamer with 5% water under high shear. Carbopol was added and blended until uniform. The total amount of PEO present in the reservoir layer is 64% wt. of the layer.

| Raw Material | % w/w |
| --- | --- |
| Testosterone, USP | 15.00 |
| PEO (PolyOx WSR N80) | 26.85 |
| PEO (PolyOx WSR 301) | 16.79 |
| Carbopol 974P | 10.00 |
| Citric Acid Monohydrate | 5.00 |
| Titanium Dioxide | 1.00 |
| Poloxamer 407 | 5.00 |

Method D.

This method is similar to that of Examples 1 and 2 and Method C of this example, with the following exceptions.

| Raw Material | % w/w |
| --- | --- |
| Testosterone, USP | 15.00 |
| Polyethylene Oxide (PolyOx WSR) | 64.00 |
| Carbopol 974P | 10.00 |
| Butylated Hydroxytoluene | 4.00 |
| Titanium Dioxide | 1.00 |
| Poloxamer 407 | 6.00 |

Method E.

This method is similar to that of Examples 1 and 2, with the following exceptions.

| Raw Material | % w/w |
| --- | --- |
| Testosterone, USP | 15.00 |
| PEO (PolyOx WSR N80) | 26.85 |
| PEO (PolyOx WSR N12K) | 18.86 |
| PEO (PolyOx WSR 301) | 16.79 |
| Carbopol 974P | 10.00 |
| Butylated Hydroxytoluene | 4.00 |

-continued

| Raw Material | % w/w |
|---|---|
| Titanium Dioxide | 1.00 |
| Poloxamer 407 | 7.50 |

The total amount of PEO present in the reservoir layer is 62.5% wt. of the layer.

Method F.

This method is similar to that of Examples 1 and 2, with the following exceptions.

| Raw Material | % w/w |
|---|---|
| Testosterone, USP | 15.00 |
| PolyOx WSR N80 | 26.85 |
| PolyOx WSR N12K | 19.36 |
| PolyOx WSR 301 | 16.79 |
| Carbopol 974P | 10.00 |
| Butylated Hydroxytoluene | 2.00 |
| Titanium Dioxide | 1.00 |
| Poloxamer 407 | 9.00 |

The total amount of PEO present in the reservoir layer is 63% wt. of the layer.

Method G.

This method is similar to that of Examples 1 and 2 and Method F of this example, with the following exceptions. In this example, the liquid medium was added as a bolus or in sequential portions to the granulation ingredients.

| Raw Material | % w/w |
|---|---|
| Testosterone, USP | 15.00 |
| Polyethylene Oxide (PolyOx WSR) | 63.00 |
| Carbopol 974P | 10.00 |
| Vitamin E | 2.00 |
| Titanium Dioxide | 1.00 |
| Poloxamer 407 | 9.00 |

Method H

The same procedure or Method G was followed except that water and alcohol (ethanol) (50:50) was used as the liquid medium for granulation.

EXAMPLE 4

Determination of Drug Stability

Twenty doses were sampled from a HME composition at the beginning, middle and end of the extrusion run a formulation. Composites of 10 doses were analyzed in duplicate for impurities by HPLC at each time point. The weight percent for each degradant was determined. Specific degradants analyzed include: 6B-Hydroxy-testosterone, 4-Androsten-16-alpha-ol-3,17-dione, Epi-Testosterone and unidentified degradants. The HPLC method employed will vary according to the drug included in the HME composition. Such methods are found in *HPLC in the Pharmaceutical Industry* (edited by Godwin W. Fong, Stanley K. Lam, New York: M. Dekker, 1991) or *HPLC Methods for Pharmaceutical Analysis* (by George Lunn and Norman R. Schmuff. New York: John Wiley & Sons, 1997), the disclosures of which are hereby incorporated by reference.

Determination of Drug Release.

Samples from the beginning, middle and end of a lot of extruded laminate (reservoir layer containing testosterone and backing layer excluding drug) were sampled and dissolution studies were conducted in 1,000 mL of Simulated Saliva Fluid (0.1% sodium lauryl sulfate at pH 6.75) at 100 rpm using the paddles. Samples were withdrawal at 1, 2, 4, 6, 8, 12 and 24 hours and assayed for testosterone content by HPLC.

EXAMPLE 5

Preparation of a Backing Film

Method A.

An exemplary backing film was prepared by hot-melt extrusion of a hydrophobic composition containing the following ingredients in the specified amounts.

| Raw Material | % w/w |
|---|---|
| PolyOx WSR N80 | 10.00 |
| PolyOx WSR 205 | 7.50 |
| PolyOx WSR 301 | 36.50 |
| Eudragit RS PO | 35.00 |
| Ethyl Cellulose Std 100 | 6.25 |
| FD&C Red 40 Lake | 0.15 |
| Titanium Dioxide | 0.60 |
| Citric Acid, monohydrate | 1.00 |
| Dibutyl Sebacate | 3.00 |

The total amount of PEO present in the backing layer is 62.5% wt. of the layer.

The backing layer formulation was modified to minimize degradation of alkaline labile drug, e.g. testosterone, at the interface between the backing layer and the reservoir layer. The backing layer formulation included citric acid and the blend was wet granulated with water to acidify the polymers. These blends were extruded as a bilayer film at a 3:1 drug layer to backing layer ratio and overall target thickness of 1.20 mm using the Randcastle coextrusion line at 135° C. maximum processing temperature. The extruder was equipped with a dual manifold flat (sheet-type) extrusion die. The moisture content of the blend prior to extrusion was 2.4%.

EXAMPLE 6

Preparation of a Bi-Layered Laminate

An exemplary bi-layered laminate comprising a backing layer and a reservoir layer was prepared by hot-melt coextrusion of a hydrophobic composition (as described in Example 5) and a hydrophilic composition, respectively, containing the following ingredients in the specified amounts.

| Reservoir Layer (Hydrophilic composition) | | |
|---|---|---|
| | % w/w | |
| Compound | Lot 1 | Lot 2 |
| Testosterone, USP | 15.00 | 15.00 |
| PolyOx WSR N80 | 26.85 | 26.85 |
| PolyOx WSR N12K | 18.36 | 18.36 |
| PolyOx WSR 301 | 16.29 | 13.79 |
| Carbopol 974P | 12.50 | 15.00 |
| Vitamin E Succinate | 3.00 | 3.00 |
| Vitamin E | 2.00 | 2.00 |

-continued

| Reservoir Layer (Hydrophilic composition) | | |
|---|---|---|
| | % w/w | |
| Compound | Lot 1 | Lot 2 |
| Titanium Dioxide | 1.00 | 1.00 |
| Poloxamer F127 | 5.00 | 5.00 |
| Total | 100.00 | 100.00 |

The films were extruded with the acidified backing film formulation as described above. The drug layer thickness was 1.10 mm and the backing film thickness was 0.40 mm. Doses were cut to provide 5.0, 7.5, 10.0, 12.5 and 15 mg Testosterone doses. The total amount of PEO present in the reservoir layer of Lot 1 is 61.5% wt. of the layer, and the total amount of PEO present in the reservoir layer Lot 2 is 59% wt. of the layer.

EXAMPLE 7

Preparation of a Bi-Layered Laminate

A clinical formulation was modified to achieve a slower dissolution profile. The testosterone concentration was lowered from 15% to 8.18% and the Carbopol concentration was increased from 10% to 15%. The batch was prepared using Diosynth sourced testosterone by wet granulation acidification with 5%, 50 mM hydrochloric acid and 5% ethanol. The granulation was coextruded with the acidified backing film. These blends were coextruded as a bi-layered laminate at a 2.75:1 drug layer to backing layer ratio and overall target thickness of 1.50 mm using the Randcastle coextrusion line at 135° C. maximum processing temperature. The moisture content of the blend prior to extrusion was 2.0%.

EXAMPLE 8

Preparation of a Bi-Layered Laminate

The methods of Examples 5 and 6 followed to prepare a bi-layered laminate comprising the following ingredients in the specified amounts. The total amount of PEO present in the reservoir layer is 65.82% wt. of the layer, and the total amount of PEO present in the backing layer is 54% wt. of the layer.

| Raw Material | % w/w |
|---|---|
| Reservoir layer | |
| Testosterone, USP | 8.18 |
| Polyethylene Oxide (PolyOx WSR) | 65.82 |
| Carbopol 974P | 15.00 |
| Vitamin E Succinate | 5.00 |
| Titanium Dioxide | 1.00 |
| Poloxamer 407 | 5.00 |
| Backing layer | |
| PolyOx WSR N80 | 10.00 |
| PolyOx WSR 205 | 7.50 |
| PolyOx WSR 301 | 36.50 |
| Eudragit RS PO | 35.00 |
| Ethyl Cellulose Std 100 | 6.25 |
| FD&C Red 40 Lake | 0.15 |
| Titanium Dioxide | 0.60 |
| Citric Acid, monohydrate | 1.00 |
| Dibutyl Sebacate | 3.00 |

EXAMPLE 9

Preparation of a Bi-Layered Laminate

The methods of Examples 5 and 6 followed to prepare a bi-layered laminate comprising the following ingredients in the specified amounts.

| Reservoir layer | |
|---|---|
| Raw Material | % w/w |
| Testosterone, USP | 8.18 |
| PolyOx WSR N80 | 23.67 |
| PolyOx WSR N12K | 20.36 |
| PolyOx WSR 301 | 16.79 |
| Carbopol 974P | 15.00 |
| Glyceryl Monooleate | 5.00 |
| Vitamin E Succinate | 5.00 |
| Titanium Dioxide | 1.00 |
| Poloxamer 407 | 5.00 |

The melt viscosity of the formulation was significantly increased as compared to another formulation containing less Carbopol. Processing conditions were modified to avoid over pressurizing the extruder. The screw speed was increased by 22% and the feed rate was decreased by 46% to achieve acceptable pressure at the adapter. The total amount of PEO present in the reservoir layer is 60.82% wt. of the layer.

EXAMPLE 10

Exemplary Method for Hot-Melt Extrusion of a Reservoir Layer

A Randcastle Taskmaster hot-melt extruder equipped with a 6 inch flat die was operated at 60-90 RPM, 6-9 Drive Amps with an Extrusion Temperatures from 65-135° C. to prepare the composition. All powders were blended in a v-shell blender prior to extrusion. Temperature zones were set as follows: zone 1: 65° C., zone 2: 120° C., zone 3: 125° C., zone 4: 135° C. die temperature 135° C. The powder blend was placed in a hopper that is located at the head of a horizontal screw such that the material is starve fed by a mass flow controller operated at 1.5 kg/hr. The residence time of the material in the extruder was approximately three to five minutes. The extrudate was cut into approximately one foot sections after exiting the die and placed on an aluminum sheets and allowed to cool at ambient conditions.

EXAMPLE 11

Exemplary Method for Hot-Melt Extrusion of a Backing Layer

A Randcastle Taskmaster hot-melt extruder equipped with a 6 inch flat die was operated at 60-90 RPM, 6-9 Drive Amps with an Extrusion Temperatures from 65-135° C. to prepare the composition. All powders were blended in a v-shell blender prior to extrusion. Temperature zones were set as follows: zone 1: 65° C., zone 2: 120° C., zone 3: 130° C., zone 4: 130° C., adapter: 135° C., transfer tube: 135° C., die temperature 140° C. The powder blend was placed in a hopper that is located at the head of a horizontal screw such that the material is starve fed by a mass flow controller operated at 0.5 kg/hr. The residence time of the material in the extruder was approximately five minutes. The extrudate was cut into approximately one-foot sections after exiting the die and placed on an aluminum sheets and allowed to cool at ambient conditions.

EXAMPLE 12

Exemplary Formulations for a Stabilized Composition of the Invention

Method A.

| Raw Material | % w/w |
| --- | --- |
| Alkaline labile drug | 0.001-50 |
| Alkaline Thermoplastic Bioadhesive Polymer | 10-99.9 |
| Acidic Component | 0.001-10 |
| Optional Hydrophilic polymer | 0-75 |
| Optional Hydrophobic polymer | 0-75 |
| Optional bioadhesive polymer | 0-50 |
| Optional Thermoplastic Polymer (or matrix-forming material) | 0-60 |
| Optional Plasticizer | 0-25 |
| Optional Antioxidant | 0-10 |
| Optional thermal lubricant | 0-20 |
| Optional Opaquant | 0-5 |

Method B.

| Raw Material | % w/w |
| --- | --- |
| Alkaline labile drug | 0.001-50 |
| PEO | 10-99 |
| Optional Hydrophilic polymer | 0-75 |
| Optional Hydrophobic polymer | 0-75 |
| Optional bioadhesive polymer | 0-50 |
| Optional Thermoplastic Polymer (or matrix-forming material) | 0-60 |
| Acidic Component | 0.001-10 |
| Optional Plasticizer | 0-25 |
| Optional Antioxidant | 0-10 |
| Optional thermal lubricant | 0-20 |
| Optional Opaquant | 0-5 |

Method C.

| Raw Material | % w/w |
| --- | --- |
| Alkaline labile drug | 0.001-50 |
| PEO | 10-99.9 |
| Optional Hydrophilic polymer | 0-75 |
| Optional Hydrophobic polymer | 0-75 |
| Polymeric Acidic Component | 0.25-35 |
| Non-polymeric acidic component | 0.001-10 |
| Optional bioadhesive polymer | 0-50 |
| Optional Thermoplastic Polymer (or matrix-forming material) | 0-60 |
| Optional thermal lubricant | 0-20 |
| Optional Antioxidant | 0-10 |
| Optional Plasticizer | 0-20 |
| Optional Opaquant | 0-5 |

One or both acidic components are present in the above formulation.

Method D.

| Raw Material | % w/w |
| --- | --- |
| Alkaline labile drug | 0.001-50 |
| PEO Grade 1 | 5-50 |
| PEO Grade 2 | 5-50 |
| PEO Grade 3 | 5-50 |
| Polymeric Acidic Component | 0.25-35 |
| Non-polymeric Acidic Component | 0.001-10 |
| Optional Hydrophilic polymer | 0-75 |
| Optional Hydrophobic polymer | 0-75 |
| Optional bioadhesive polymer | 0-50 |
| Optional Thermoplastic Polymer (or matrix-forming material) | 0-60 |
| Optional Thermal Lubricant | 0-20 |
| Optional Plasticizer | 0-20 |
| Optional Antioxidant | 0-10 |
| Optional Opaquant | 0-5 |

Three different grades of PEO are present in the above formulation. One or both acidic components are present in the above formulation.

Method E.

| Raw Material | % w/w |
| --- | --- |
| Alkaline labile drug | 0.001-50 |
| PEO Grade 1 | 5-50 |
| PEO Grade 2 | 5-50 |
| PEO Grade 3 | 5-50 |
| CARBOPOL | 0.25-35 |
| Non-polymeric Acidic Component | 0.001-10 |
| POLOXAMER | 0.25-20 |
| Optional Hydrophobic polymer | 0-75 |
| Optional Bioadhesive Polymer | 0-50 |
| Optional Thermoplastic Matrix-Forming Material | 0-60 |
| Optional Thermal Lubricant | 0-20 |
| Optional Plasticizer | 0-20 |
| Optional Antioxidant | 0-10 |
| Optional Opaquant | 0-5 |

The formulation comprises three different grades of PEO, a polymeric acidic component, a non-polymeric organic acid, a hydrophilic polymer, an alkaline labile drug, and optionally one or more the other components listed in the above table.

EXAMPLE 13

Exemplary Formulations for a Backing Layer of the Invention

Method A.

| Raw Material | % w/w |
| --- | --- |
| Thermoplastic Polymer | 10-99.9 |
| Hydrophobic polymer | 0.1-99.9 |
| Optional Hydrophilic polymer | 0-50 |
| Optional Thermoplastic Polymer | 0-75 |
| Optional Acidic Component | 0-10 |
| Optional Plasticizer | 0-20 |
| Optional Antioxidant | 0-10 |
| Optional thermal lubricant | 0-20 |
| Optional Opaquant | 0-5 |

Method B.

| Raw Material | % w/w |
| --- | --- |
| Polyethylene Oxide | 5-99.9 |
| Hydrophobic polymer | 0.1-99.9 |
| Optional Hydrophilic polymer | 0-50 |

-continued

| Raw Material | % w/w |
| --- | --- |
| Optional Thermoplastic Polymer | 0-75 |
| Optional Acidic Component | 0-10 |
| Optional Plasticizer | 0-20 |
| Optional Antioxidant | 0-10 |
| Optional thermal lubricant | 0-20 |
| Optional Opaquant | 0-5 |

Method C.

| Raw Material | % w/w |
| --- | --- |
| PEO Grade 1 | 5-50 |
| PEO Grade 2 | 5-50 |
| PEO Grade 3 | 5-50 |
| Hydrophobic polymer | 0.1-99.9 |
| Optional Hydrophilic polymer | 0-50 |
| Optional Thermoplastic Polymer | 0-75 |
| Optional Acidic Component | 0-10 |
| Optional Plasticizer | 0-20 |
| Optional Antioxidant | 0-10 |
| Optional thermal lubricant | 0-20 |
| Optional Opaquant | 0-5 |

Three different grades of PEO are present and the hydrophobic polymer is also present.

Method D.

| Raw Material | % w/w |
| --- | --- |
| PEO Grade 1 | 5-50 |
| PEO Grade 2 | 5-50 |
| PEO Grade 3 | 5-50 |
| Polyacrylate polymer | 10-85 |
| Ethyl Cellulose | 1-85 |
| Optional Thermoplastic Polymer | 0-75 |
| Optional Acidic Component | 0-10 |
| Optional Plasticizer | 0-20 |
| Optional Antioxidant | 0-10 |
| Optional thermal lubricant | 0-20 |
| Optional Opaquant | 0-5 |

Three different grades of PEO are present.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed:

1. A bi-layered hot-melt laminate made by a process comprising the steps of:
    a) wet or dry granulating at least one water swellable or water soluble alkaline matrix-forming material comprising poly(ethylene oxide) (PEO); at least one acidic component; and optionally one or more antioxidants, one or more hydrophobic polymers, one or more hydrophilic polymers, one or more other excipients, or a combination thereof to form an excipient mixture having a solution pH of 7 or less;
    b) mixing the excipient mixture with an alkaline labile drug to form a bioadhesive thermoplastic hydrophilic composition;
    c) hot-melt extruding the hydrophilic composition to form the bioadhesive hot-melt extruded composition,
    d) hot-melt extruding a second composition; and
    e) laminating the bioadhesive hot-melt extruded composition and second composition together to form a bioadhesive bi-layered hot-melt laminate comprising a bioadhesive hydrophilic reservoir layer and a hydrophobic low permeability backing layer, respectively, wherein the thermoplastic second composition comprises at least one hydrophobic polymer, optionally a plasticizer, optionally one or more hydrophilic polymers, and optionally at least one acidic component, wherein the second composition excludes a drug.

2. The process of claim 1, wherein the PEO is selected from the group consisting of PEO grade 1, PEO grade 2, PEO grade 3, and a combination thereof,
    wherein PEO Grade 1 is polyethylene oxide with a solution viscosity in the range of 12-8800 mPa☐s at 25 °C. in a 5% solution or with an approximate molecular weight range from 100,000-600,000; PEO Grade 2 is polyethylene oxide with a solution viscosity in the range of 8800 mPa☐S at 25 °C. in a 5% solution to 4000 mPa☐s at 25 °C. in a 2% solution or with an approximate molecular weight range from 900,000-2,000,000; and PEO Grade 3 is polyethylene oxide with a solution viscosity in the range of 1650-15,000 mPa☐s at 25 °C. in a 1% solution or with an approximate molecular weight range from 4,000,000-8,000,000.

3. The process of claim 2, wherein the PEO comprises two or more grades of PEO selected from the group consisting of PEO Grade 1, PEO Grade 2, and PEO Grade 3.

4. The process of claim 2, wherein the PEO comprises PEO Grade 1, PEO Grade 2, and PEO Grade 3.

5. The process of claim 1, wherein the hot-melt extruding step comprises coextruding the bioadhesive hot-melt extruded composition and a thermoplastic hydrophobic second composition to form a bioadhesive bi-layered hot-melt coextruded laminate comprising a bioadhesive hydrophilic reservoir layer and a hydrophobic low permeability backing layer, respectively, wherein the thermoplastic hydrophobic second composition comprises at least one hydrophobic polymer, optionally a plasticizer, optionally one or more hydrophilic polymers, and optionally at least one acidic component, wherein the second composition excludes a drug.

6. The process of claim 5, wherein the granulation step is wet granulation and the wet granulation is conducted with water, buffer, an aqueous organic solvent, or a combination thereof.

7. The process of claim 1, wherein the granulation step is wet granulation and the wet granulation is conducted with water, buffer, an aqueous organic solvent, or a combination thereof.

8. The process of claim 1, wherein the at least one acidic component is selected from the group consisting of a polymeric organic acid, a non-polymeric organic acid, an inorganic acid, an acidic polymer, and a combination thereof.

9. The process of claim 1, wherein the water swellable or water soluble alkaline matrix-forming material comprises one or more antioxidants selected from the group consisting of ascorbic acid, ascorbyl palmitate, butylated hydroxyanisole, butylated hydroxytoluene, hypophosphorous acid, monothioglycerol, sodium ascorbate, sodium formaldehyde sulfoxylate, sodium metabisulfite, vitamin C, sodium bisulfite, vitamin E and its derivatives, propyl gallate, and a combination thereof.

10. The process of claim 1, wherein the alkaline labile drug is selected from the group consisting of testosterone, oxybutynin, morphine, fentanyl, aspirin, lansoprazole, omeprazole, pantoprazole, rabeprazole, naltrexone, benzocaine, penicillin G, noradrenaline, isoprenaline, thiamine and atracurium.

11. A bioadhesive hot-melt extruded composition made by the process of claim 1.

12. A bi-layered hot-melt laminate made by the process of claim 5.

13. The bi-layered hot-melt laminate of claim 12, wherein the laminate is in a dosage form adapted for transdermal, transmucosal, rectal, pulmonary, nasal, vaginal, ocular, or otic drug delivery, or as an implantable drug delivery device.

14. The bi-layered hot-melt laminate of claim 1, wherein the laminate is in a dosage form adapted for transdermal, transmucosal, rectal, pulmonary, nasal, vaginal, ocular, or otic drug delivery, or as an implantable drug delivery device.

15. The process of claim 1, wherein the alkaline labile drug is testosterone.

\* \* \* \* \*